US011092580B2

(12) United States Patent
Ratcliffe et al.

(10) Patent No.: US 11,092,580 B2
(45) Date of Patent: Aug. 17, 2021

(54) DIAGNOSTIC APPARATUS

(71) Applicants: UNIVERSITY OF THE WEST OF ENGLAND, BRISTOL, Bristol (GB); THE UNIVERSITY OF BRISTOL, Bristol (GB)

(72) Inventors: Norman Ratcliffe, Bristol (GB); Benjamin Paul Costello, Bristol (GB); Richard Ewen, Bristol (GB); Christopher Probert, Bristol (GB)

(73) Assignees: UNIVERSITY OF THE WEST OF ENGLAND, BRISTOL, Bristol (GB); THE UNIVERSITY OF BRISTOL, Bristol (GB)

( * ) Notice: Subject to any disclaimer, the term of this patent is extended or adjusted under 35 U.S.C. 154(b) by 0 days.

(21) Appl. No.: 16/805,590

(22) Filed: Feb. 28, 2020

(65) Prior Publication Data

US 2020/0200721 A1 Jun. 25, 2020

Related U.S. Application Data

(63) Continuation of application No. 13/510,692, filed as application No. PCT/EP2010/067859 on Nov. 19, 2010, now abandoned.

(30) Foreign Application Priority Data

Nov. 20, 2009 (GB) ...................... 0920315

(51) Int. Cl.
*G01N 30/78* (2006.01)
*G01N 30/74* (2006.01)
(Continued)

(52) U.S. Cl.
CPC ............. *G01N 30/78* (2013.01); *G01N 30/74* (2013.01); *G01N 33/0034* (2013.01);
(Continued)

(58) Field of Classification Search
CPC .... G01N 30/78; G01N 30/74; G01N 33/0034; G01N 2030/009; G01N 2030/067;
(Continued)

(56) References Cited

U.S. PATENT DOCUMENTS 6,289,288 B1 9/2001 Kraft
6,341,520 B1 1/2002 Satoh et al.
(Continued)

FOREIGN PATENT DOCUMENTS

EP 0 317 299 A2 5/1989
EP 0 926 492 A1 6/1999
(Continued)

OTHER PUBLICATIONS

Siripatrawan, Ubonrat. "Rapid differentiation between *E. coli* and *Salmonella typhimurium* using metal oxide sensors integrated with pattern recognition." Sensors and Actuators B: Chemical 133.2 (2008): 414-419. (Year: 2008).*
(Continued)

*Primary Examiner* — Robert J Eom
(74) *Attorney, Agent, or Firm* — Maschoff Brennan

(57) ABSTRACT

A diagnostic apparatus for analysing a sample to diagnose disease, the apparatus comprising: a separating element for separating gas derived from the sample into component parts; a sensor arrangement coupled to the separating element such that a component part of the gas is directed towards the sensor arrangement, the sensor arrangement being configured to detect compounds which may be indicative of disease; and a processing element coupled to an output of the sensor arrangement, the processing element being configured to process a signal output by the sensor arrangement to provide a diagnosis.

9 Claims, 12 Drawing Sheets

(51) Int. Cl.
*G01N 30/06* (2006.01)
*G01N 30/00* (2006.01)
*G01N 30/88* (2006.01)
*G01N 33/00* (2006.01)

(52) U.S. Cl.
CPC . *G01N 2030/009* (2013.01); *G01N 2030/067* (2013.01); *G01N 2030/8813* (2013.01); *G01N 2333/205* (2013.01); *G01N 2800/26* (2013.01); *G01N 2800/342* (2013.01)

(58) Field of Classification Search
CPC ..... G01N 2030/8813; G01N 2333/205; G01N 2800/26; G01N 2800/342
See application file for complete search history.

(56) References Cited

U.S. PATENT DOCUMENTS

| | | |
|---|---|---|
| 2002/0144537 A1 | 10/2002 | Sharp et al. |
| 2002/0182739 A1 | 12/2002 | Sadik et al. |
| 2003/0039299 A1 | 2/2003 | Horovitz et al. |
| 2009/0155125 A1 | 6/2009 | Michiue et al. |
| 2009/0275852 A1 | 11/2009 | Oki et al. |
| 2011/0259080 A1 | 10/2011 | Ratcliffe et al. |

FOREIGN PATENT DOCUMENTS

| | | |
|---|---|---|
| GB | 2 364 571 A | 1/2002 |
| WO | 00/54050 A2 | 9/2000 |
| WO | 01/55714 A1 | 8/2001 |

OTHER PUBLICATIONS

Kohl, D., et al. "Systematic studies on responses of metal-oxide sensor surfaces to straight chain alkanes, alcohols, aldehydes, ketones, acids and esters using the SOMMSA approach." Sensors and Actuators B: Chemical 70.1-3 (2000): 43-50. (Year: 2000).*

Tischner, A. et al., "Ultrathin Sn02 gas sensors fabricated by spray pyrolysis for the detection of humidity and carbon monoxide," Sensors and Actuators B: Chemical, vol. 134, No. 2, pp. 796-802 (2008).

De Lacy Costello, B. P. J. et al., "Thick film organic vapour sensors based on binary mixtures of metal oxides," Sensors and Actuators B: Chemical, Vil. 92, Issue 1-2, pp. 159-166 (2003).

Kim, K. W. et al., "The selective detection of C2H50H using Sn02—Zn0 thin film gas sensors prepared by combinatorial solution deposition," Sensors and Actuators B: Chemical, vol. 123, No. 1, pp. 318-324 (2007).

Zampolli, S. et al., "Selectivity enhancement of metal oxide gas sensors using a micromachined gas chromatographic column," Sensors and Actuators B: Chemical, vol. 105, No. 2, pp. 400-406 (2005).

Hong, H. K. et al., "Gas identification using micro gas sensor array and neural-network pattern recognition," Sensors and Actuators B: Chemical 33, Issue 1-3, pp. 68-71 (1996).

Barsan, N. and Weimar, U., "Understanding the fundamental principles of metal oxide based gas sensors; the example of CO sensing with Sn02 sensors in the presence of humidity," Journal of Physics: Condensed Matter, vol. 15, No. 20, pp. R813-R839 (2003).

Kuhara, T., "Diagnosis and monitoring of inborn errors of metabolism using urease-pretreatment of urine, isotope dilution, and gas chromatography-mass spectrometry," Journal of Chromatography B, vol. 781, Issue 1-2, pp. 497-517 (2002).

Nilsson, A. et al., "Quantitative determination of volatile organic compounds in indoor dust using gas chromatography-UV spectrometry," Environment International, vol. 31, Issue 8, pp. 1141-1148 (Oct. 2005).

Garner, C. E. et al., "Volatile organic compounds from feces and their potential for diagnosis of gastrointestinal disease," The FASEB Journal, vol. 21, No. 8, pp. 1675-1688 (Jul. 2007).

Turner, A. P. F. and Magan, N., "Electronic noses and disease diagnostics," Nature Reviews Microbiology, vol. 2, pp. 161-166 (2004).

The Editors of Encyclopaedia Britannica, "Gas Chromatography," Encyclopcedia Britannica Inc., retrieved from http://www.britannica.com/EBchecked/topic/226369/gas-chromatography, retrieved on Feb. 27, 2020, pp. 2.

United Kingdom Intellectual Property Office, Search Report for GB 0920315.9 dated Mar. 19, 2010, 5 pages.

* cited by examiner

Two-dimensional plot of the derived discriminant scores of VOC data from the stools of asymptomatic volunteers (●), patients with Campylobacter jejuni (▲), patients with ulcerative colitis (□), and patients with Clostridium difficile (○) infections.

DIAGNOSTIC APPARATUS

The present application relates to a diagnostic apparatus for analysing a sample to diagnose disease, and to a method of diagnosing disease using such an apparatus.

Infectious diseases such as *Clostridium difficile* (*C. difficile*), Norovirus, cholera and *Campylobacter* can spread rapidly, causing distress and even morbidity to those affected and considerable difficulty and expense to public health authorities treating patients and attempting to manage outbreaks of such diseases. A major problem in outbreak management is that there is often a delay between disease symptoms being presented and a diagnosis being made, due to time-consuming diagnostic techniques requiring manual laboratory analysis of samples, for example stool samples, provided by patients. In some cases the results of such analysis may not be available for up to five days, leading to unnecessarily long delays in diagnosing the patient. Until an accurate diagnosis is made, effective treatment of the patient can be difficult, which can lead to deterioration in the patient's condition and prolonged and unnecessary suffering to the patient. Additionally, whilst the patient is awaiting diagnosis, the disease is able to spread through contact with the patient by medical staff, relatives and the like, or by airborne transmission. Thus, delays in diagnosing infectious diseases can lead to a widespread outbreak of disease.

Non-infectious diseases can also be diagnosed by analysis of a sample provided by a patient. For example, prostate cancer is usually diagnosed by a combination of techniques such as digital rectal examination, a test for serum prostate specific antigen (PSA) and trans-rectal ultrasound-guided prostate biopsy. Worldwide, the use of serum levels of PSA as a screening test remains controversial due to its low specificity (38%) and the acknowledged high rate of false negative results (up to 20% with PSA level <4 ng ml$^{-1}$). Digital rectal examination and trans-rectal ultrasound-guided prostate biopsy are invasive procedures which are stressful to the subject and may deter patients from presenting for testing.

In view of this, there is a need for a highly sensitive, specific, non-invasive and cost-effective diagnostic system for diagnosing disease quickly and easily at the point of care of the patient.

Efforts have been made to develop diagnostic techniques whereby disease can be diagnosed quickly and accurately by analysing samples such as stool samples, urine samples or the like via analysis of volatile biomarkers. However, these efforts have not been successful to date and have been hampered by technical difficulties such as the high moisture content of samples and the presence in the samples of sulphides which are damaging to sensors. More important, however, is the difficultly in selecting how to analyse the samples. For example, it has been shown experimentally that stool samples can contain a large number of different volatile organic compounds (VOCs); across a cohort study of stool samples provided by 30 donors, 297 different VOCs were identified in the stool samples. Determining which of these compounds and substances could be indicative of disease represents a major challenge which has hitherto not been overcome.

According to a first aspect of the invention there is provided a diagnostic apparatus for analysing a sample to diagnose disease, the apparatus comprising: a separating element for separating gas derived from the sample into component parts; a sensor arrangement coupled to the separating element such that a component part of the gas is directed towards the sensor arrangement, the sensor arrangement being configured to detect a compound which may be indicative of disease; and a processing element coupled to an output of the sensor arrangement, the processing element being configured to process a signal output by the sensor arrangement to provide a diagnosis.

The diagnostic apparatus of the present invention permits rapid and accurate diagnosis by detecting compounds or groups of compounds present in the sample which are indicative of disease. The apparatus can be provided as a stand alone device which can be installed in hospitals, doctors' surgeries and other medical facilities to permit fast, accurate diagnosis at the point of care, allowing a doctor, nurse or other medical practitioner to begin effective treatment quickly and to put in place any measures which may be necessary to prevent or restrict the spread of disease. The sample may be a sample of a bodily fluid such as urine or saliva, or may be a sample of a solid or semi-solid such as faeces. Alternatively or additionally the sample may comprise a gas evolved from a liquid or solid such as urine or faeces.

The separating element may comprise a multi-capillary column.

Alternatively or additionally, the separating element may comprise a single-capillary column, or may comprise a plurality of single-capillary columns.

The sensor arrangement may comprise one or more sensors selected from the group comprising a metal-oxide sensor, a UV sensor and an ammonia or amine sensor.

In this context, the term "metal oxide sensor" refers to a sensor which uses a heated metal oxide element to detect certain volatile compounds, whilst the term "UV sensor" refers to a sensor which uses an ultraviolet or near ultraviolet light activated metal oxide element to detect certain volatile compounds. The term "ammonia or amine sensor" refers to a sensor that detects ammonia or amines.

Preferably the sensor arrangement comprises two or more sensors arranged in a serial configuration.

Alternatively, the sensor arrangement may comprise two or more sensors arranged in a parallel configuration.

The sensor arrangement may be configured to detect one or more volatile compounds present in the gas. For example, the sensor arrangement may be configured to detect one or more volatile organic compounds in the gas.

The sensor arrangement may be configured to generate a signal indicative of the elution time of a volatile compound in the sample.

The processing element may be configured to compare the signal generated by the sensor arrangement to a known profile from one or more previously-diagnosed samples.

The apparatus may further comprise a pre-treatment stage for altering physio-chemical parameters of the sample.

The apparatus may further comprise heating means for heating the sample to promote the release of the gas.

The apparatus may further comprise means for acidifying or basifying the sample, to alter the number or concentration of volatile compounds detected by sensor arrangement.

The processing element may implement an artificial neural network to provide the diagnosis.

According to a second aspect of the invention there is provided a method of diagnosing disease by analysing a sample, the method comprising the steps of: collecting the sample; separating a gas derived from the sample into component parts; directing a component part of the gas towards a sensor arrangement, the sensor arrangement being configured to detect a compound which may be indicative of disease; and processing a signal output by the sensor arrangement to provide a diagnosis.

The step of separating the gas may comprise passing the gas through a separating element comprising a multi-capillary column.

Alternatively, the step of separating the gas may comprise passing the gas through a separating element comprising a single-capillary column or a plurality of single-capillary columns.

The sensor arrangement may comprise one or more sensors selected from the group comprising a metal-oxide sensor, a UV sensor and an ammonia or amine sensor.

Preferably, the sensor arrangement comprises two or more sensors arranged in a serial configuration.

Alternatively, the sensor arrangement may comprise two or more sensors arranged in a parallel configuration.

The sensor arrangement may be configured to detect one or more volatile compounds present in the gas.

The sensor arrangement may be configured to detect one or more volatile organic compounds present in the gas.

The sensor arrangement may be configured to generate a signal indicative of the elution time of a volatile compound in the sample.

The step of processing the signal output by the sensor arrangement may comprise comparing the signal generated by the sensor arrangement to a known profile from one or more previously-diagnosed samples.

The method may further comprise pre-treating the sample to alter physio-chemical parameters of the sample.

The method may further comprise heating the sample to promote the release of the gas.

The method may further comprise acidifying or basifying the sample to alter the number or concentration of volatile compounds detected by sensor arrangement.

The step of processing the signal output by the sensor arrangement may comprise processing the signal using an artificial neural network to provide the diagnosis.

According to a third aspect of the invention there is provided an ammonia or amine sensor comprising a light source which emits light in the visible range and a photodetector, the light source being arranged to emit light towards a detecting surface of the photodetector in operation of the ammonia or amine sensor, wherein an ammonia- or amine-sensitive substance having an optical property which changes in the presence of ammonia or an amine is disposed in an optical path between the light source and the detecting surface.

One of the detecting surface and the light source may be at least partially coated in the ammonia- or amine-sensitive substance.

Alternatively, the ammonia or amine sensor may further comprise a substantially transparent medium which is at least partially coated in the ammonia- or amine-sensitive substance, the substantially transparent medium being disposed in the optical path between the light source and the detecting surface of the photodetector.

The optical transmissivity of the ammonia- or amine-sensitive substance may decrease in the presence of ammonia The ammonia- or amine-sensitive substance may comprise a pH-sensitive dye in a solution mixed with a polymer material.

The pH-sensitive dye may be bromophenol blue.

The polymer material may comprise polyvinylpyrrolidone, for example.

The light source may be selected so as to have a peak wavelength which falls within a main pass band of the ammonia- or amine-sensitive substance in the absence of ammonia.

For example, the light source may have a peak wavelength of around 602 nm.

The light source may comprise an LED.

The photodetector may comprise a photodiode.

The ammonia or amine sensor may further comprise a second light source, the second light source being selected so as to have a peak wavelength which falls within a main pass band of the ammonia- or amine-sensitive substance in the presence of ammonia or amine.

For example, the second light source may have a peak wavelength of around 432 nm.

The light source and the second light source may be arranged to be actuated in an alternating manner.

The second light source may be arranged to emit light towards the detection surface of the photodetector in operation of the ammonia or amine sensor.

Embodiments of the invention will now be described, strictly by way of example only, with reference to the accompanying drawings, of which:

Figure 1:
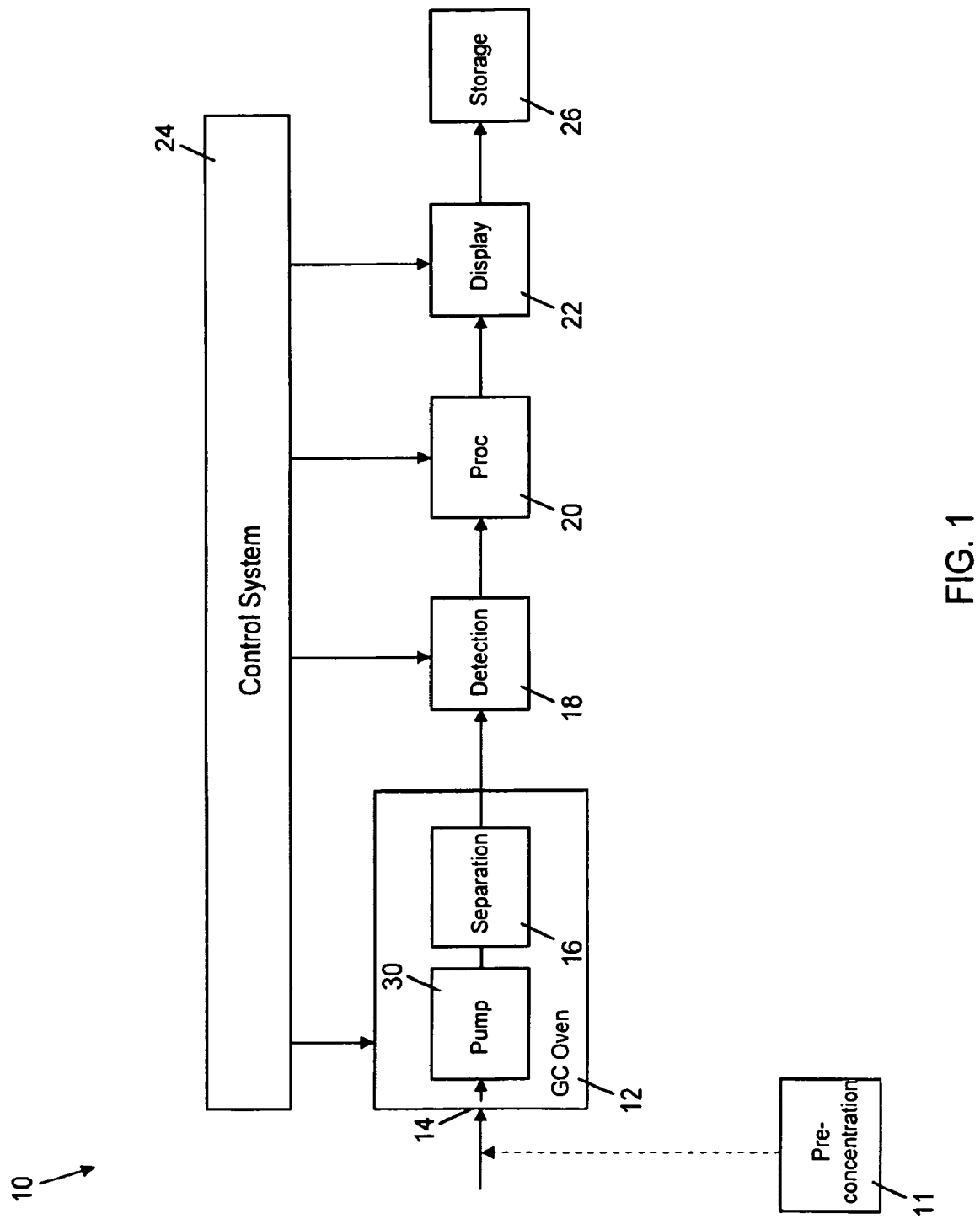
FIG. 1 is a schematic representation of a diagnostic apparatus.

Referring first to FIG. 1, a diagnostic apparatus is shown in schematic form at 10. The apparatus 10 has a gas chromatography oven 12 with an inlet port 14 through which gas evolved from a sample of a bodily fluid supplied by a patient can be injected into an inlet of one or more separating columns housed in the gas chromatography oven 12. In some embodiments the inlet port 14 communicates directly with an outlet of a container in which the sample is stored and in which the sample may be heated, to a temperature of around 60° C. for example (although other temperatures may also be suitable), to release the gas, whilst in other embodiments the storage and collection of gas is performed elsewhere, for example in a headspace vial with an integrated septum from which gas can be collected in a syringe and subsequently injected or pumped into the gas chromatography oven 12 through the inlet port 14.

It has been found that embodiments in which the inlet port 14 communicates directly with the outlet of the sample container gives rise to significant improvements in performance compared to embodiments in which the gas is injected or pumped into the gas chromatography oven 12 through the inlet port.

This is because in these "closed loop" embodiments a series of valves can be used to extract the gas evolved from the sample using clean air. The gas collected in this way can then be directed to a separation stage 16, which is described in more detail below. Moreover, in closed loop embodiments in which the inlet port 14 communicates directly with the outlet of the sample container there is less scope for loss of the sample, as the sample is provided directly to the inlet port rather than being drawn into a syringe, which is typically at room temperature, before being transferred to the inlet port 14 of the gas chromatography oven 12. Additionally, in the "closed loop" embodiments where the inlet port 14 communicates directly with the outlet of the sample container all of the components of the sampling system can be maintained at high temperatures (e.g. around 90-100° C.).

In some embodiments of the apparatus 10, a pre-treatment stage 11 may be provided, to alter the psysio-chemical parameters of the sample to optimise the relative concentrations of volatile compounds in the gas evolved from the sample for diagnostic purposes. For example, in the pre-treatment stage 11 volatile compounds from the gas evolved from the sample may be collected in one or more solid-phase microextration (SPME) fibres to concentrate the volatile compounds, which fibre(s) are then introduced into the inlet port 14 and heated to cause the organic compounds collected in the SPME fibre(s) to desorb from the fibre(s). Gas evolved from the sample may also be collected and stored using Automated Thermal Desorption tubes may be similarly introduced into the inlet port 14. Additionally or alternatively, the pre-treatment stage 11 may include a heated water bath or other heating means to heat the sample to promote or accelerate the release of gas. The pre-treatment stage 11 may include means for acidifying or basifying the sample prior to collecting the gas, to alter the number and/or concentration of volatile compounds evolved from the sample. For example, the pre-treatment stage 11 may include one or more injectors for injecting a predetermined quantity of an acid (e.g. sulphuric acid) or a base (e.g. sodium hydroxide) into the container in which the sample is stored. The pre-treatment stage 11 may be integral with other stages of apparatus 10, or may be provided as a dedicated device which is separate from the other stages of the apparatus 10. Moreover, the pre-treatment stage 11 may have a number of discrete sub-stages, for example a heating sub-stage, a concentration stage and an acidification or basification stage.

The apparatus 10 may include a pump 30 which supplies an air flow to carry the gas around the apparatus 10. In the embodiment illustrated in FIG. 1 the pump 30 supplies air from an exterior of the apparatus 10. The applicant has found that sensors used in the apparatus 10 (which sensors are described in detail below) function optimally in air. Additionally, air is readily available and requires no bulky cylinders for storage. To prevent airborne volatile compounds and other contaminants from the environment in which the apparatus 10 is installed from interfering with the operation of the apparatus 10 a filter such as a charcoal filter or an activated charcoal filter is provided at the or each outlet of the pump 30 of this embodiment such that the air pumped around the apparatus 10 is filtered prior to exiting the pump 30. The flow rate of the filtered air may be around 200 ml/minute. It will be appreciated, of course, that other types of filter may be employed for the purpose of filtering the air. In other embodiments the pump 30 may include an inlet through which a carrier gas such as purified helium may be introduced, which carrier gas may carry the gas evolved from the sample around the apparatus 10.

An inlet 14 of the gas chromatography oven 12 communicates with a separating stage 16 which is made up of one or more separating columns. In the embodiment illustrated in FIG. 1 the separating stage 16 is housed within the oven 12. This arrangement provides a stable temperature for the separating stage 16 so that elution times for volatile compounds contained in the gas evolved from the sample remain the same regardless of any differences in the temperature of the environment in which the apparatus 10 is operating. The inlet 14 of the separating stage may be contained within the oven 12, or may be external to the oven 12. The temperature of the inlet 14 is independent of the temperature of the oven 12, and may be adjusted independently of the temperature of the gas chromatography oven 12. The applicant has found that an inlet temperature of 100° C. and an oven temperature of between 30° C.-40° C. produce good results.

In one embodiment two 30 metre capillary columns are used in the separating stage 16, with the outlet of each column being divided into two such that the separated components of the gas arrive simultaneously at four outlets.

In an alternative embodiment a multi-capillary column having a length of around 0.5 metres is used in the separating stage 16. It will be appreciated, however, that different lengths and configurations of column can be used, and indeed a plurality of multi-capillary columns can be used. For example, the separating stage may include a single-capillary column or a plurality of single-capillary columns of the same or different lengths.

The multi-capillary column used in this example may have around 1200 separate capillaries. An advantage of using such a multi-capillary column in the separating stage is that it is capable of quickly separating volatile compounds such as volatile organic compounds in the gas. For example, volatile compounds from stool samples can be separated in around 5 minutes. The multi-capillary column can also be used at room temperature, whilst its small size is advantageous as it allows the apparatus 10 to be small and portable such that it can easily be accommodated at a point of patient care such as a doctors' surgery, clinic or the like.

The separation stage 16 may be varied to change its separation characteristics, for example to change the elution time of certain volatile compounds. An inside wall of the capillaries of the separation stage 16 (whether single capillary columns, as used in the first embodiment described above, or a multi-capillary column, as used in the alternative embodiment described above) is coated with a thin layer of a stationary phase, and the thickness and chemical properties of this stationary phase coating affect the separating capabilities of the capillary, for example by altering the elution time of certain compounds. In certain applications of the apparatus 10 it may be beneficial to use a plurality of capillaries, each having a different inner stationary phase coating, in the capillaries of the separating stage 16, to improve the differentiating ability of the apparatus 10, thereby improving the capability of the apparatus 10 to diagnose disease accurately.

The outlet(s) of the separating stage 16 are coupled to one or more inlets of a detection stage 18 which is configured to detect one or more volatile compounds present in the gas derived from the sample. The detection stage 18 includes one or more sensors for sensing particular volatile compounds or groups of volatile compounds, as is discussed in more detail below. In one embodiment an array of sensors is provided, the array containing one or more of each of a metal-oxide sensor, a UV sensor and an ammonia or amine sensor.

The sensor(s) of the detection stage 18 may be housed in a container which is positioned inside the gas chromatography oven 12. The container may be made of aluminium, or any other suitable material. The container should be electrically isolated from electronic components of the sensor(s) of the detection stage 18 to avoid any risk of unwanted electrical connections between electronic components. Housing the sensor(s) of the detection stage 18 in a separate container in this way ensures that the sensor(s) are maintained in constant environmental conditions, which helps to improve the response and stability of the sensor(s). Additionally, the container in which the sensor(s) of the detection stage 18 are housed helps to isolate the sensors from potentially interfering volatiles from other components of the apparatus 10.

The sensor(s) of the detection stage 18 produce electrical outputs which change when a volatile compound is detected. The outputs of the sensor(s) of the detection stage 18 are connected to a processor 20 which is operative to interpret the output(s) of the sensor(s) to determine whether volatile compounds which are indicative of disease are present in the gas derived from the sample, and to provide a diagnosis of the disease on a display 22 of the apparatus 10. The operation of the processor 20 is described in more detail below.

The operation of the apparatus 10 is controlled by a control system 24, and the apparatus 10 may have a storage device 26 such as a hard disc drive, non-volatile memory or an optical storage device such as a CD or DVD recorder or the like for storing and retrieving different diagnostic programs (as is discussed in more detail below) and for storing diagnoses and other results produced by the apparatus 10. Alternatively, the diagnostic programs, diagnoses and other results may be stored in memory in the processor 20, the control system 24 or both. Suggested treatment plans may also be stored in the storage device 26, processor 20 or control system, each treatment plan being associated with a particular diagnosis such that on successful diagnosis by the apparatus 10 a suggested treatment plan is provided with the diagnosis.

Figure 2:
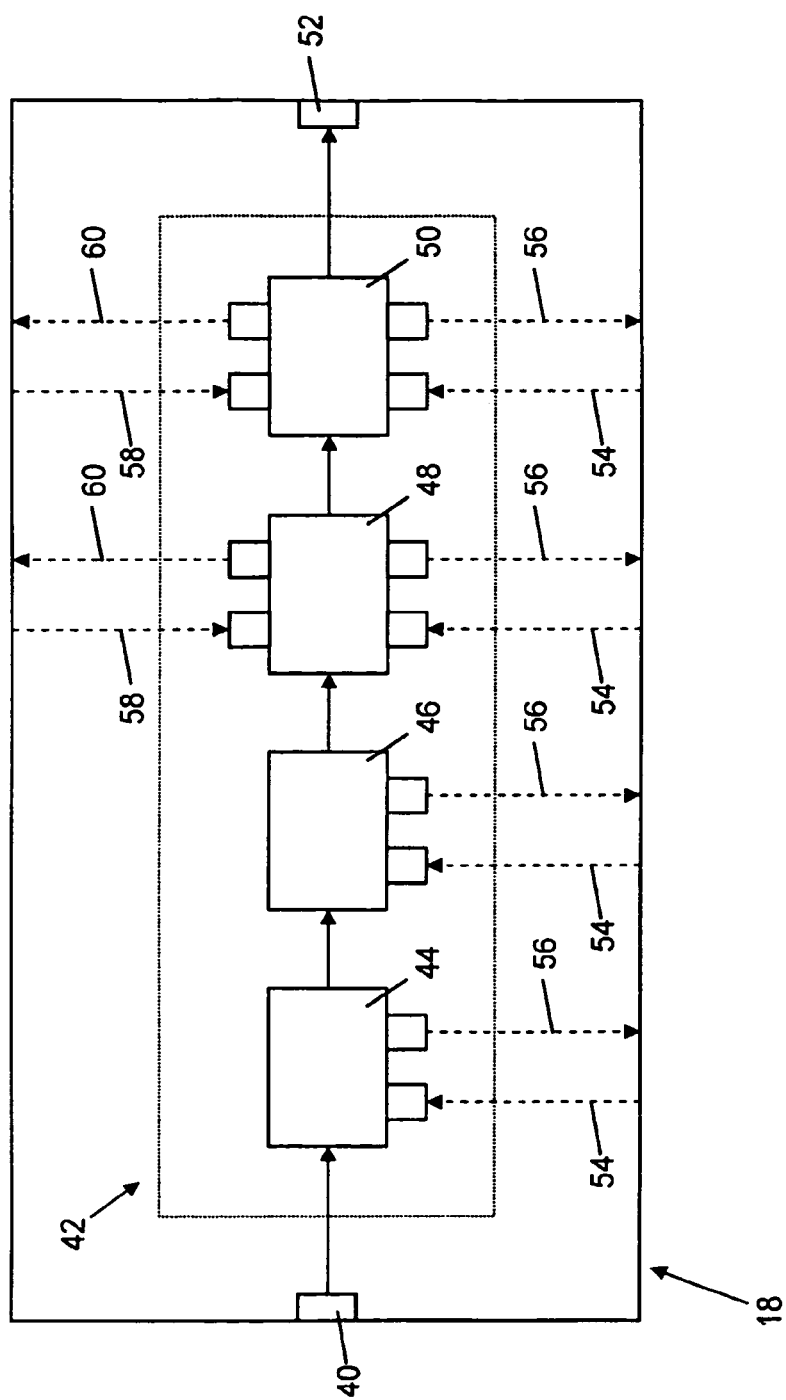
FIG. 2 is a schematic representation of an embodiment of a detection stage of the diagnostic apparatus of FIG. 1.

FIG. 2 is a schematic representation of a detection stage 18 used in an embodiment of the apparatus 10. In this embodiment the separation stage 16 has a single outlet which communicates with an inlet 40 of the detection stage 18 through which volatile compounds from the gas derived from the sample are directed to a sensor array, which is shown in dotted outline at 42 in FIG. 2. The sensor array 42 in this example includes four sensors: an ammonia or amine sensor 44 (of a type described in more detail below), a sensor 46 (of a type that will be familiar to those skilled in the art) which uses an ultraviolet (or near ultraviolet) light activated metal oxide element at room temperature to detect certain volatile compounds (hereinafter referred to as a UV sensor) and sensors 48, 50 of a type described below which use a heated metal oxide element to detect certain volatile compounds (hereinafter referred to as heated metal oxide sensors 48, 50). It will be appreciated, however, that other gas sensors could be used in the sensor array 42 of the apparatus 10, alongside or in place of one or more of the sensors 44, 46, 48, 50.

The sensors 44, 46, 48, 50 are arranged in a serial configuration such that volatile compounds passing from the inlet 40 to an outlet 52 of the detection stage pass each sensor 44, 46, 48, 50 in sequence. As is described in more detail below, the heated metal oxide sensors 48, 50 include heaters which heat the sensors 48, 50 to temperatures in the range of 300° C. 600° C. These temperatures are sufficient to destroy any viruses or other microbiological contaminants that may be present in the volatile compounds entering the detection stage 18. Thus, placing these sensors at the end of the flow path for the volatile compounds in the detection stage 18 ensures that any viruses present in the volatile compounds are destroyed before any exhaust gas is exhausted through the outlet 52 of the detection stage 18.

The sensors 44, 46, 48, 50 each have a control input 54 through which control signals from the control system 24 can be received to control the operation of the sensors 44, 46, 48, 50 and a signal output 56 for transmitting output signals to the processor 20 and control system 24. The output signals may be conditioned by a pre-processing stage, or may be transmitted directly to the processor 20 for processing. The metal oxide sensors 48, 50 also have temperature control signal inputs 58 by means of which the control system 24 can control the temperature of the sensor 48, 50, whilst temperature measurement outputs 60 provide signals indicative of the temperature of the sensors 48, 50 to the control system 24.

Figure 3:
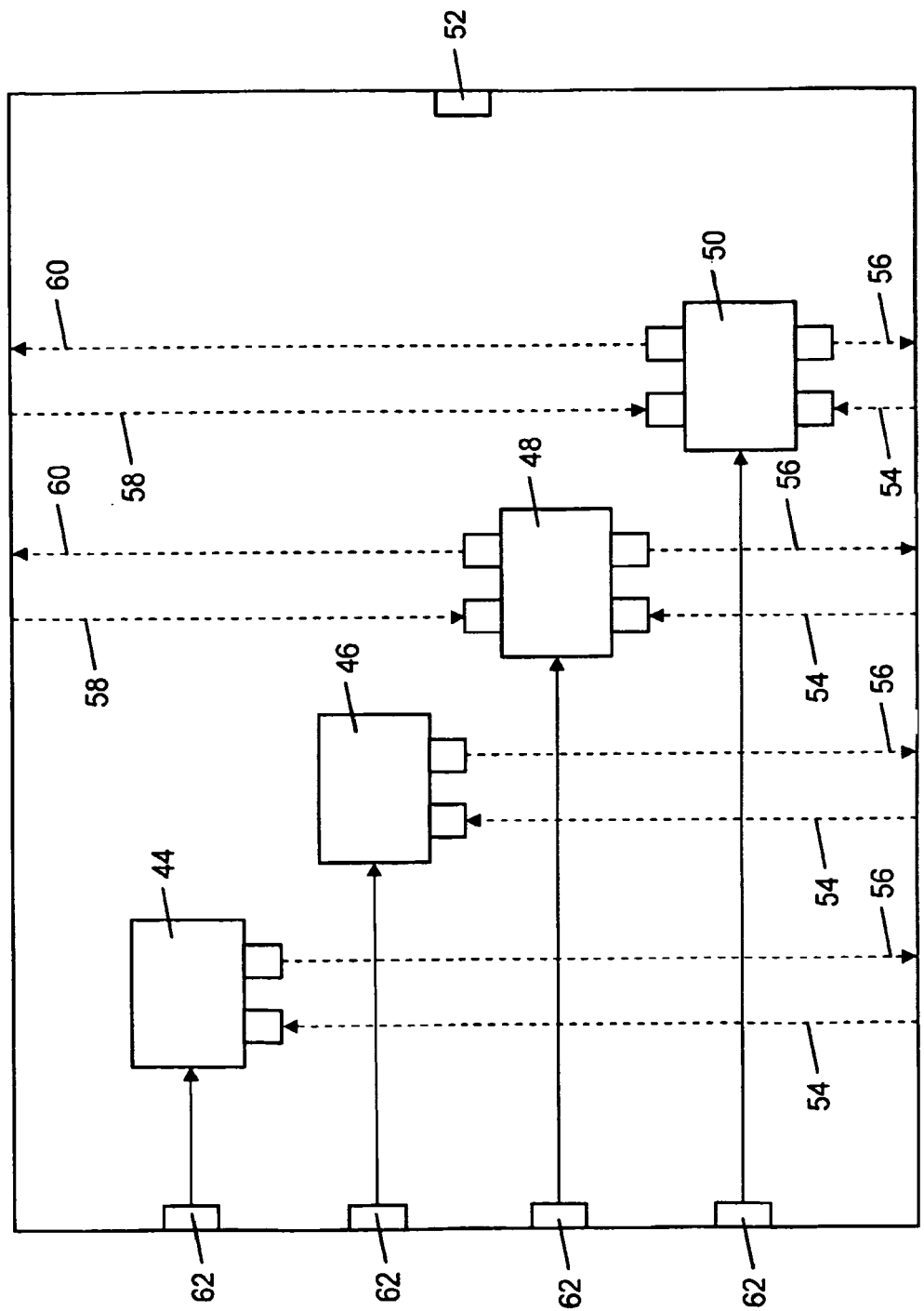
FIG. 3 is a schematic representation of an alternative embodiment of a detection stage of the diagnostic apparatus of FIG. 1.

An alternative arrangement of the detection stage 18 is illustrated in FIG. 3, in which the same reference numerals are used to identify elements common to the embodiments of FIGS. 2 and 3. In the arrangement shown in FIG. 3, the separating stage 16 has four output columns which each communicate with a respective inlet 62 of the detection stage 18. The inlets 62 are each coupled to a respective one of the sensors 44, 46, 48, 50 in a parallel configuration. The arrangement of FIG. 3 suffers from a reduction in sensitivity in comparison to that shown in FIG. 2, as the flow of volatile compounds is split, whilst there is an increased risk that viruses and the like present in the volatile compounds may not be destroyed prior to being exhausted through the exhaust port 52, as not all of the volatile compound streams pass over the heated metal oxide sensors 48, 50.

Figure 4:
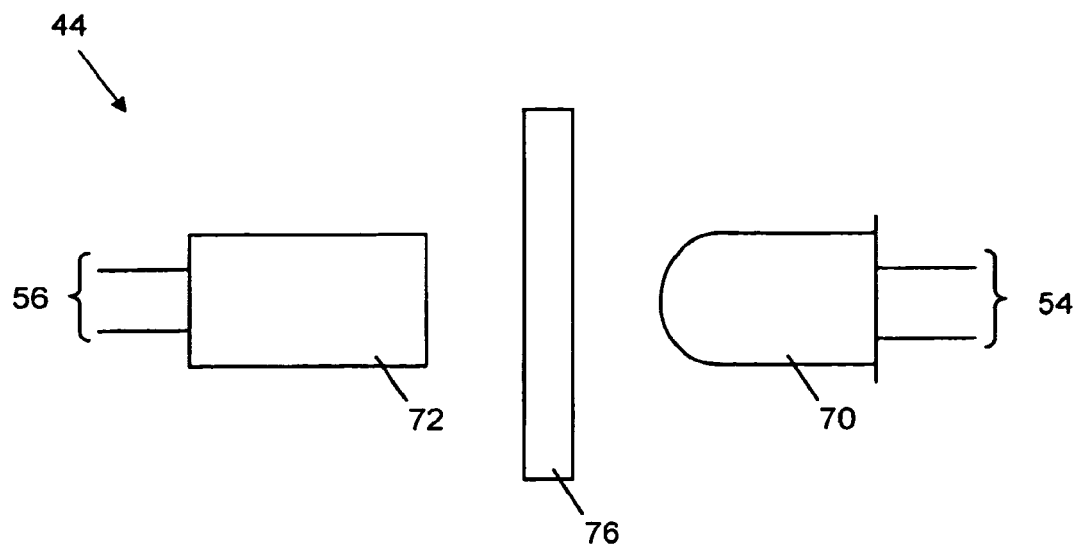
FIG. 4 is a schematic representation of an ammonia or amine sensor used in certain embodiments of the diagnostic apparatus shown in FIG. 1.

An ammonia or amine sensor 44 is illustrated schematically in FIG. 4, and comprises a visible light source 70, which in this example is an orange light emitting diode (LED) having a peak wavelength of 602 nm, and a photodetector 72, which in this example is an amplified photodiode. The LED 70 and photodiode 72 are arranged such that light emitted by the LED is directed towards a detecting surface of the photodiode 72. An ammonia- or amine-sensitive material 74, which in this example is an ammonia- or amine-sensitive dye film consisting of a pH-sensitive dye such as bromophenol blue in a solution mixed with polyvinylpyrrolidone, is disposed between the LED 70 and the detecting surface of the photodiode 72. The ammonia- or amine-sensitive dye film 74 may be deposited directly onto one or both of the LED 70 and the detecting surface of the photodiode 72, or may be provided on a substantially transparent medium 76 disposed in an optical path between the LED 70 and the detecting surface of the photodiode 72.

In operation of the ammonia or amine sensor 44, a control signal is received from the control system 54 to actuate the light source 70. The photodetector 72 detects the light from the light source 70 and outputs a voltage in the range 0 to 2.5V, which output voltage is dependent on the intensity of light received by the photodetector 72. In this example, when no ammonia or amine is present, the ammonia- or amine-sensitive material 74 has a peak transmittivity at 606 nm, and thus allows substantially all the light from the light source 70 to pass to the photodetector 72, such that the photodetector produces a high output voltage (e.g. at or close to 2.5V). However, where ammonia or amine is present, the optical transmittivity at 606 nm of the ammonia- or amine-sensitive material 74 is reduced, having in this example a peak transmittivity at 432 nm. Thus, the intensity of light received by the photodetector 72 is reduced and the output voltage of the photodetector 72 is reduced. The output of the photodetector 72 is passed to the processor 20 (with or without pre-processing) which processes the output signal in conjunction with signals output by the other sensors 46, 48, 50 to determine if volatile compounds present in the gas derived from the sample supplied by the patient are indicative of disease. It will of course be appreciated that the ammonia- or amine-sensitive material may have different optical properties to those mentioned in the example above, such that the range of optical wavelengths it passes in the absence of ammonia or amine and the range of optical wavelengths it passes in the presence of ammonia or amine may be different, and a light source having a peak wavelength that falls within the pass band of the ammonia- or amine-sensitive material in the absence of ammonia but outside of the pass band of the ammonia- or amine-sensitive material in the presence of ammonia or amine should be used.

Figure 5:
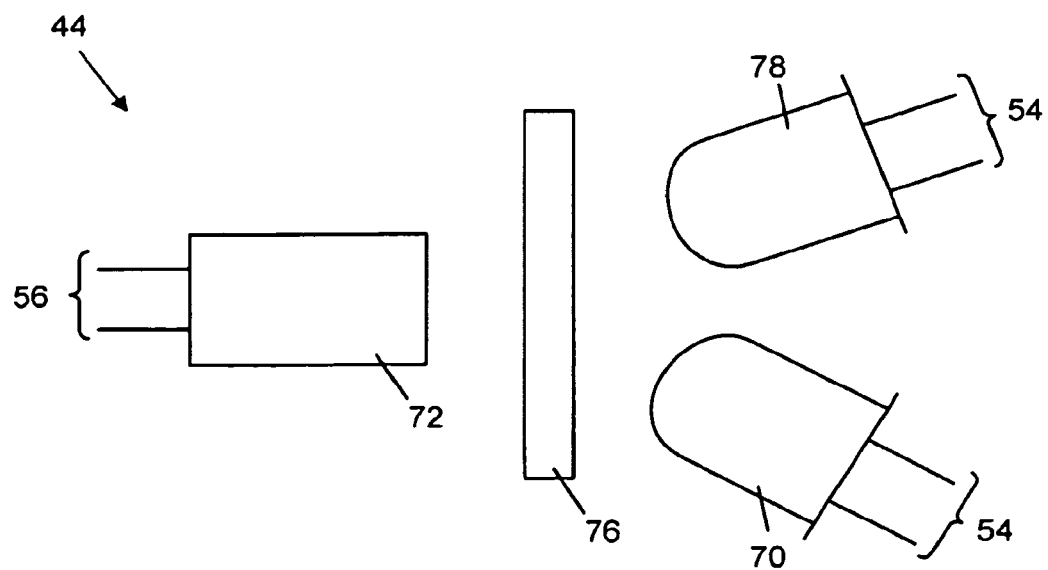
FIG. 5 is a schematic representation of an alternative embodiment of an ammonia or amine sensor used in certain embodiments of the diagnostic apparatus shown in FIG. 1.

An alternative embodiment of an ammonia or amine sensor 44 is illustrated in FIG. 5, in which the same reference numerals are used to identify elements common to the embodiments of FIGS. 4 and 5. In this embodiment a second LED 78 which emits blue light having a peak wavelength in the 432 nm range, that is to say within the main pass band of the ammonia- or amine-sensitive material in the presence of ammonia or amine, is provided as well as the LED 70 which emits orange light having a peak wavelength in the 602 nm range.

The LEDs 70, 78 are arranged such that light emitted by both LEDs 70, 78 is incident on the photodetector 72. An ammonia- or amine-sensitive material 74, which in this example is an ammonia- or amine-sensitive dye film consisting of a pH-sensitive dye such as bromophenol blue in a solution mixed with polyvinylpyrrolidone, is disposed between the LED 70 and the detecting surface of the photodiode 72. The ammonia- or amine-sensitive dye film 74 may be deposited directly onto the LEDs 70, 78 or the detecting surface of the photodiode 72 or both, or may be provided on a substantially transparent medium 76 disposed in an optical path between the LEDs 70, 78 and the detecting surface of the photodiode 72.

In operation of this embodiment of the ammonia or amine sensor 44, a control signal is received from the control system 54 to actuate the LEDs alternately, to ensure that there is no crosstalk between the two LEDs 70, 78. The photodetector 72 detects the light from the LEDs 70, 78 and outputs a voltage in the range 0 to 2.5V, which output voltage is dependent on the intensity of light received by the photodetector 72. In this embodiment, when no ammonia or amine is present, the ammonia- or amine-sensitive material 74 has a peak transmittivity at 606 nm, and thus allows substantially all the light from the orange LED 70 to pass to the photodetector 72, whilst reducing the intensity of the light received from the blue LED 78 by the photodetector 72. Thus, in the absence of ammonia or amine the photodetector 72 produces a high output voltage (e.g. at or close to 2.5V) when the orange LED 70 is actuated. Where ammonia or amine is present, the optical transmittivity of the ammonia- or amine-sensitive material 74 is reduced, having in this example a peak transmittivity at 432 nm. Thus, the intensity of light received from the orange LED 70 by the photodetector 72 is reduced, whilst the intensity of light received by the photodetector 72 from the blue LED 78 increases. Thus, in the presence of ammonia the photodetector 72 produces a high output voltage when the blue LED 78 is actuated. The output of the photodetector 72 is measured by the processor 20 in synchronisation with the alternate actuation of the orange and blue LEDs 70, 72 to provide an indication of the optical transmittivity of the ammonia- or amine-sensitive dye film 74 when each of the LEDs 70, 78 is actuated. This allows the optical transmittivity of the ammonia- or amine-sensitive dye film 74 to be measured for both light sources 70, 78 using a single photodetector 72. This embodiment of the ammonia or amine sensor 44 is advantageous in that it is able to provide an indication of a fault with the sensor 44. If the photodetector 72 were partially obscured or darkened for a reason other than exposure to ammonia or amine the transmittivity of the ammonia- or amine-sensitive dye film 74 would decrease at both the 602 nm and the 432 nm wavelength (i.e. when either LED 70, 78 is actuated). Thus, if a decrease in the optical transmittivity of the ammonia- or amine-sensitive film 74, as indicated by the output voltage of the photodetector 72 when each of the LEDs 70, 78 is actuated, is detected for both wavelengths it is clear that there is a fault with the sensor 44.

Instead of providing only a single photodetector 72, the alternative ammonia or amine sensor 44 may be provided with a second photodetector in a sealed light-tight chamber with the blue LED 78. However, this arrangement requires further splitting of the flow of volatile compounds, which is undesirable for the reasons explained above.

Figure 6:
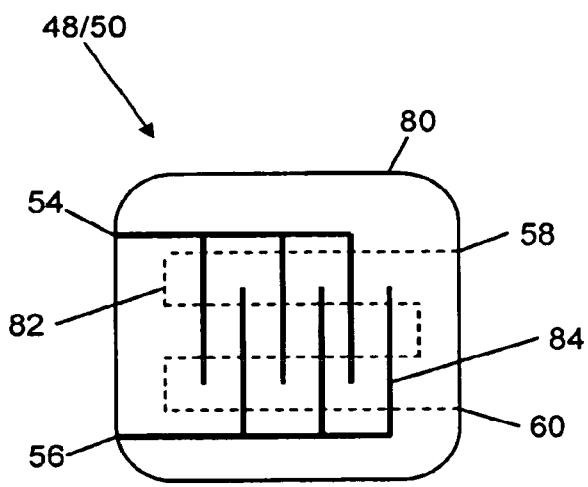
FIG. 6 is a schematic representation of a heated metal oxide sensor used in certain embodiments of the diagnostic apparatus shown in FIG. 1.

FIG. 6 is a schematic illustration of a heated metal oxide sensor 48, 50 used in the detection stage 18. The heated metal oxide sensor 48, 50 comprises a substrate 80 of alumina having on one side thereof a platinum heater 82, which is shown in dashed lines in FIG. 5. A plurality (six in this example) of interdigitated gold electrodes 84 is provided on the other side of the substrate 80, and a sensor film is applied to the interdigitated gold electrodes 84. The sensor film in this example is made from a paste made up of equal masses of zinc oxide and tin oxide powders mixed in water. Alternatively the sensor film can be made from a paste comprising a non-aqueous binder with equal masses of zinc oxide and tin oxide.

A current is applied to the platinum heater 82 to achieve a desired operating temperature of the sensors 48, 50. In the example shown in FIGS. 2 and 3, one of the metal oxide sensors 48, 50 operates at a temperature of 400° C., whilst the other metal oxide sensor 50, 48 operates at a temperature of 450° C. The operating temperature of the metal oxide sensors 48, 50 determines their selectivity and sensitivity to volatile compounds, and these operating temperatures have been found to provide a suitable level of selectivity and sensitivity. The control system 24 controls the operating temperature of the metal oxide sensors 48, 50 by measuring the resistance of the platinum heater 82 and comparing the measured resistance of the platinum heater 82 with the resistance required at the desired temperature (by consulting a look-up table, for example) and adjusting the current applied to the platinum heater 82 to achieve the required resistance and hence the desired temperature.

In use of the heated metal oxide sensor 48, 50, a voltage is applied to the sensor film and the current flowing through the sensor film is measured. The current flowing through the sensor film varies depending upon the presence of volatile compounds. Thus, a particular measured current may be interpreted as being indicative of the presence of a particular volatile compound.

The measured current in the metal oxide sensors 48, 50 is converted into a voltage between 0 and 2.5V and this voltage is passed to the processor 20 (with or without pre-processing), which processes this output signal in conjunction with signals output by the other sensors 46, 48 to determine if volatile compounds present in the gas derived from the sample supplied by the patient are indicative of disease.

The metal oxide sensors 48, 50 are operable at temperatures as low as 150° C., and the control system 24 is able to control their operating temperatures according to the application for which the apparatus 10 is to be used. For example, the metal oxide sensors 48, 50 may be most sensitive to volatile compounds which are indicative of a particular disease at one operating temperature, and most sensitive to other volatile compounds that are indicative of a different disease at a different operating temperature. By changing the operating temperature of the metal oxide sensors 48, 50 according to the particular application for which the apparatus 10 is to be used, diagnostic accuracy and effectiveness can be optimised. The applicant has found, however, that at temperatures of 300° C. and below the response of the metal oxide sensors 48, 50 can be masked due to the presence of water eluting from the separating stage 16, which can cause smaller output signals which may be indicative of the presence of particular volatile compounds to be obscured. Temperatures in the range 400° C. to 500° C. have been found to be particularly suitable.

It will be appreciated that the sensors 44, 46, 48, 50 have a finite lifespan. It is anticipated that the sensors 44, 46, 48, 50 used in the embodiments described herein will have a lifespan in excess of one year, but this will depend to some extent upon the number of diagnosing operations performed by the apparatus 10. To facilitate maintenance of the apparatus 10 the sensors 44, 46, 48, 50 may be implemented as separate modules which can be replaced individually when necessary. To this end, the sensor modules may be provided with quick-release connectors by means of which they can be connected to and disconnected from the detection stage 18.

The processor 20 may include an analogue to digital converter (ADC) to convert the voltages supplied by the outputs of the sensors 44, 46, 48, 50 into digital signals which can be used by the processor. Alternatively, the sensor output signals may be pre-processed to convert the output voltages into a digital format.

The processor 20 is programmed to produce, from the outputs of the sensors 44, 46, 48, 50, a trace of voltage, current or resistance versus time for each of the sensors 44, 46, 48, 50. These traces include peaks at certain times (as different volatile compounds elute from the separating stage 16 at different times), indicating when particular volatile compounds were detected by the sensors 44, 46, 48, 50. In one embodiment, the processor 20 compares these traces to known traces or profiles from one or more previously-diagnosed samples containing particular volatile compounds or combinations of volatile compounds which are indicative of particular diseases. If the processor 20 identifies a correlation between the traces produced from a current sample and those associated with a particular disease, a diagnosis of that disease can be made and displayed on the display 22. As is discussed above, a suggested treatment plan may be associated with each disease such that when the processor 20 identifies a correlation or other relationship between the traces produced by the current sample and those associated with the disease and diagnoses the disease a suggested treatment plan can be displayed with the diagnosis, to allow a health professional to begin treatment of the patient without delay.

In another embodiment, an artificial neural network (ANN) is used to analyse the traces produced from the output of the sensors 44, 46, 48, 50 to diagnose particular diseases based on the volatile compounds detected by the sensors 44, 46, 48, 50 of the detection stage 18.

Figure 7:
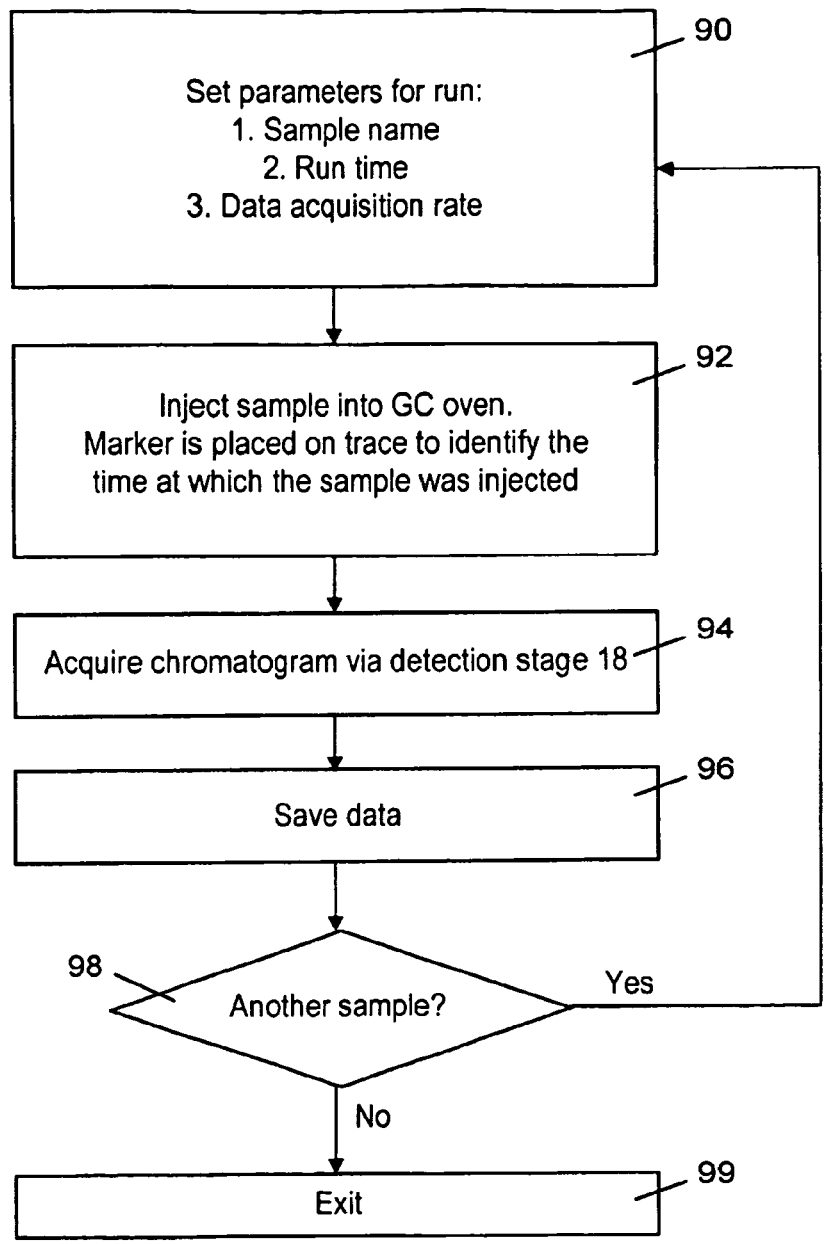
FIG. 7 is a flow diagram illustrating a process for acquiring data to train an artificial neural network used in certain embodiments of the apparatus shown in FIG. 1.

FIG. 7 is a flow diagram illustrating a process for acquiring data to train the ANN used to analyse the traces to diagnose disease based on the volatile compounds detected by the sensors 44, 46, 48, 50 of the detection stage 18.

At step 90 initial parameters for a data acquisition run are set. These parameters include the sample name, the duration of the data acquisition run, and the data acquisition rate. The data acquisition rate can be set at any appropriate value, but it has been found that a rate of between two and five readings or data samples per second gives rise to good results, as unresolved or overlapping peaks representing the different volatile compounds emerging from the separating stage 16 can be observed, as will be explained in more detail below.

At step 92 a patient sample is injected into the gas chromatography oven 12 and a marker is placed on the traces produced by the processor 20 from the outputs of the sensors 44, 46, 48, 50 so that the time at which the sample was injected can be identified.

At step 94 a chromatogram is acquired from the detection stage 18 as a series of data points, each of which represents an output of a sensor 44, 46, 48, 50. With a data acquisition rate of 2 readings or data samples per second 2 data points of the chromatogram are produced in each one second interval. These data points are saved at step 96, and a test is made at step 98 to determine whether another sample is to be injected to the apparatus 10. If a further sample is to injected processing returns to step 90, whilst if no further sample is to be injected the process stops at step 99.

Figure 8:
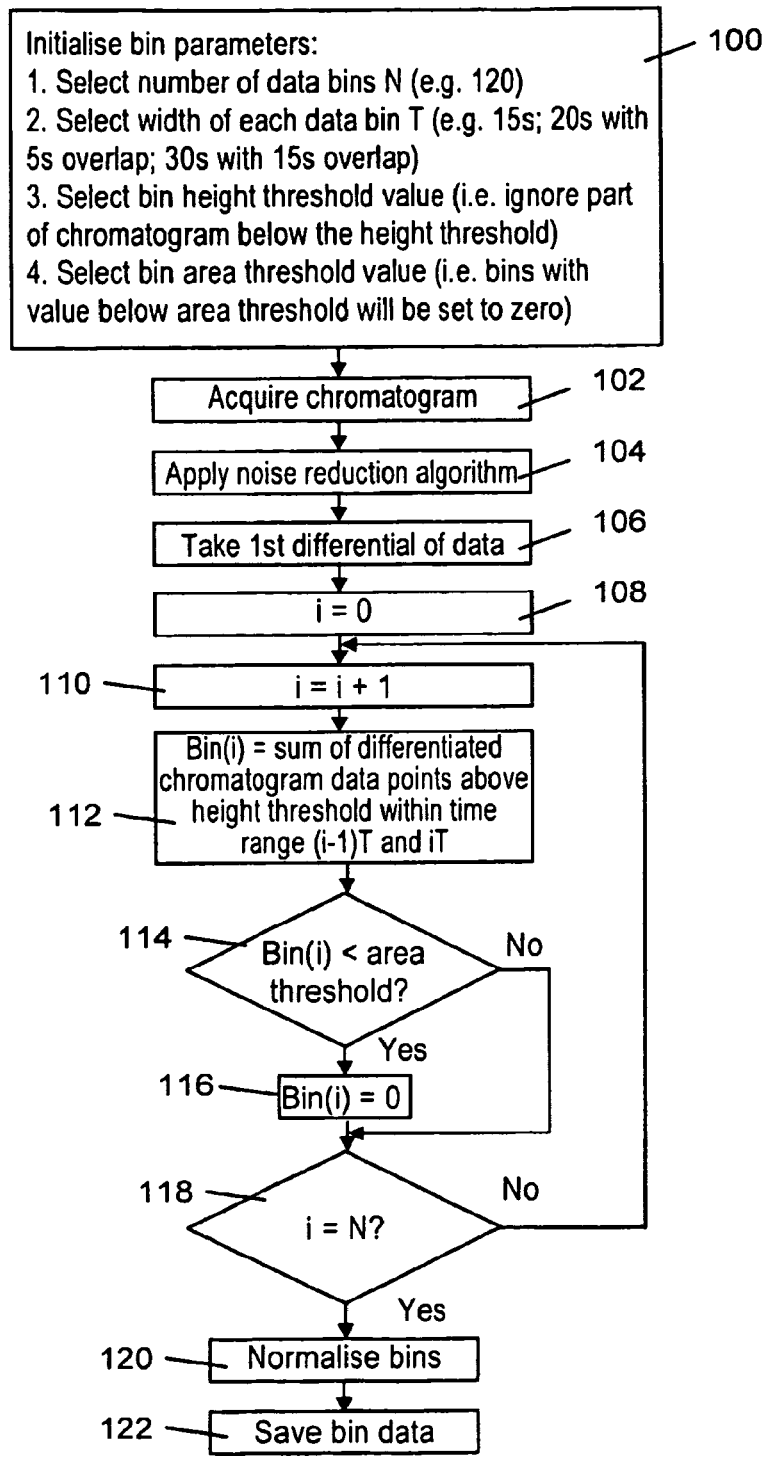
FIG. 8 is a flow diagram illustrating a process used to produce data bins for use in the artificial neural network used in certain embodiments of the apparatus shown in FIG. 1.

In a typical data acquisition run of 30 minutes, 3600 data points will be collected (120 samples/minute×30 minutes). To simplify the input of the saved data to the ANN, the number of data points is reduced by dividing the time axis of the chromatogram into regular time intervals T, which may be, for example, 15 seconds long. The processed chromatogram data is summed over each of these intervals. One time interval containing the summed values is referred to as a 'bin'. FIG. 8 is a flow diagram illustrating a process used to produce the bins.

At step 100 the bin parameters, such as the number bins N, the width of each bin (e.g. a 15 second bin or a 20 second bin with a 5 second overlap), the bin height (which is a threshold below which data can be disregarded as noise) and a bin area threshold are defined and initialised.

At step 102 the chromatogram is acquired, and a noise reduction algorithm is applied at step 104. The first differential of the chromatogram with respect to time, $dR/dt$ (where R is the resistance the sensor at time t) is taken at step 106, by subtracting the value of each data point by that of the preceding data point and dividing the result by the time interval between the data point and the preceding data point, and a loop counter i is initiated at step 108. A processing loop is then entered at step 110 in which a bin value for each bin is calculated by summing the differentiated chromatogram data points above the preset height threshold within the time of the respective bins. If the calculated bin has an area less than the preset threshold its value is set to 0. This process is repeated for all N data bins.

Once all of the bins have been calculated, they are normalised at step 120 and the normalised bin data is saved at step 122.

Figure 9:
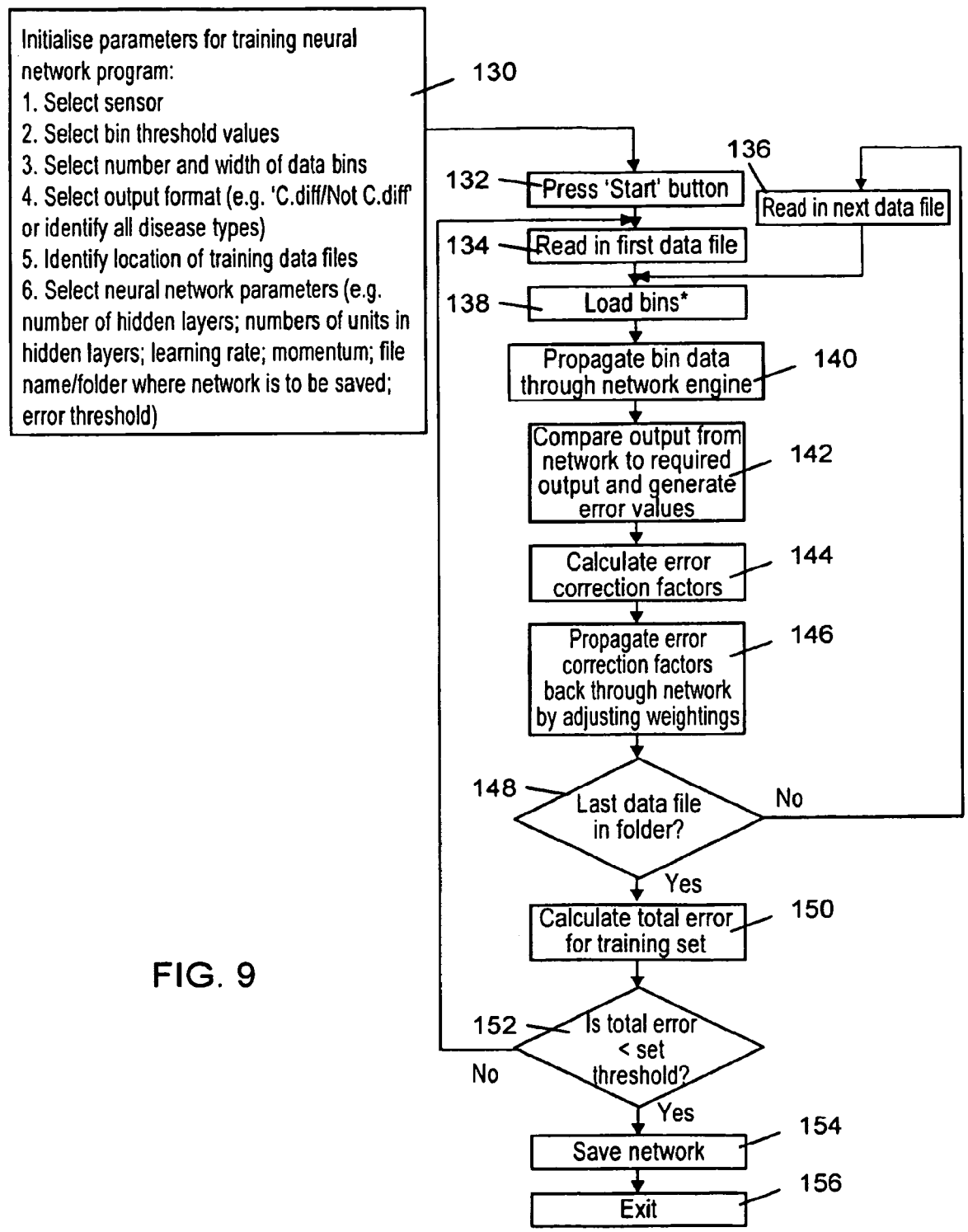
FIG. 9 is a flow diagram illustrating a training process for the artificial neural network used in certain embodiments of the apparatus of FIG. 1.

FIG. 9 is a flow diagram illustrating a training process for the ANN. At step 130 training parameters for the ANN are initialised. For example, a sensor may be selected, the bin threshold values and the number and width of the data bins (discussed above) are input. An output format (e.g. diagnosis of a particular disease or identification of all disease types) is selected. The location of training data is identified and parameters of the neural network are selected.

The training process begins at step 132 and a first data file containing training data is loaded at step 134. The data bins are loaded at step 138 and the bin data is propagated through the network engine at step 140. At step 142 the output from the ANN is compared to a required output and error values are generated. Error correction factors are calculated at step 144 and are propagated back through the ANN at step 146 by adjusting weightings. At step 148 a test is made to determine whether the data file currently being processed is the last data file. If not, the next data file is read (at step 136) and processing returns to step 138. If the current data file is the last data file, a total error for the training set is calculated at step 150. At step 152 a test is made to determine whether the total error is below a threshold. If not the processing returns to step 134 and the training data is re-entered. If the total error is below the threshold the network is saved at step 154 and can subsequently be used by the apparatus 10 for real-time diagnosis of disease from a sample of a bodily fluid provided by a patient.

Figure 10:
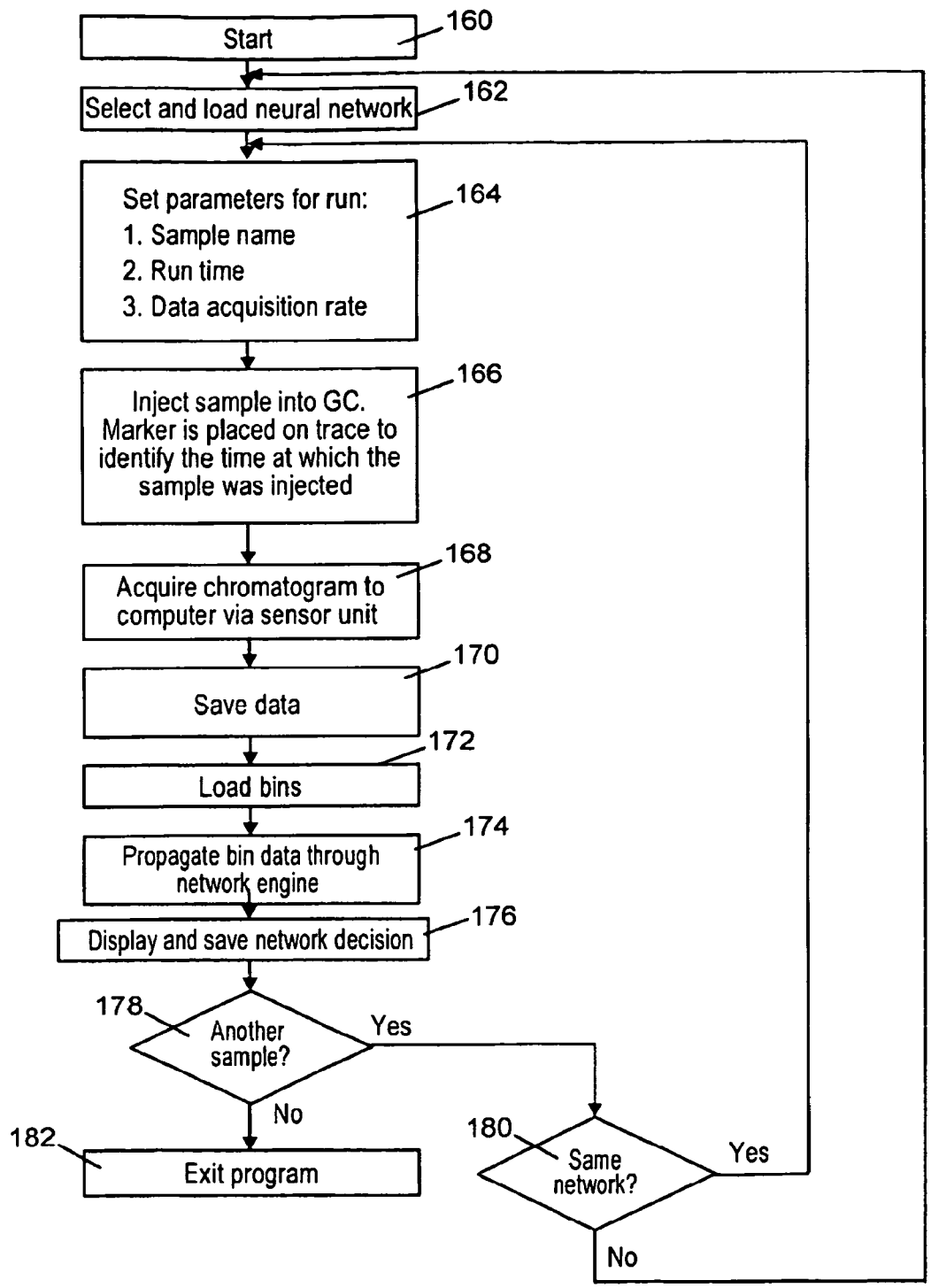
FIG. 10 is a flow diagram illustrating a process used by the artificial neural network used in certain embodiments of the apparatus of FIG. 1 to make a real-time diagnosis of a disease.

FIG. 10 is a flow diagram illustrating the process used by the ANN of the apparatus 10 to make a real-time diagnosis of a disease. The process starts at step 160, and at step 162 an appropriate ANN is selected and loaded. Run parameters including sample name and run time are set at step 164. A sample is injected into the gas chromatography oven 12 at step 166, and a chromatogram is acquired by the sensors 44, 46, 48, 50 of the detection stage 18 in step 168. The data is saved at step 170 and is loaded into data bins at step 172. The bin data is propagated through the entire ANN at step 174 and a decision is produced by the ANN, to produce a diagnosis, which is displayed on the display 22 of the apparatus 10 and saved at step 176. A test is made at step 178 to determine whether another sample is to be analysed. If not, the process ends at step 182. If another sample is to be analysed, a test is made at step 180 to determine whether the same ANN is to be used. If so, processing recommences at step 164. If not, a new ANN is selected and loaded at step 162 before processing recommences at step 164.

It will be appreciated that other pattern recognition methodologies may be used in the apparatus 10 instead of or alongside an ANN to diagnose disease on the basis of volatile compounds detected by the detection stage 18. For example, the processor could implement a canonical, Fourier transformation, wavelet transformation, Bayesian, principal component analysis (PCA), or k-nearest neighbour (KNN) pattern recognition algorithm, or a statistical fixed algorithm, threshold or Boolean algorithm.

The apparatus 10 can be used to diagnose gastro-intestinal disease such as *C. difficile*, Norovirus, *Campylobacter, Salmonella* and the like by taking a stool sample from a patient, analysing it to identify volatile compounds contained in the gas derived from the sample and using the comparison method or the ANN method described above.

The apparatus 10 can also be used to diagnose other conditions by analysing other bodily fluid. For example, urine samples can be analysed to diagnose renal disease and other conditions, whilst breath samples can be analysed to diagnose lung disease.

Whilst the apparatus 10 of the present invention is described as having four sensors 44, 46, 48, 50, it will be appreciated that more, fewer, or different combinations of sensors can be used. For example, in a device designed solely to diagnose *C. difficile* by analysing gas derived from stool samples provided by patients, only a combination of an ammonia or amine sensor 46 and a single heated metal oxide sensor 48, 50 may be provided. Where a combination of two or more sensors including a heated metal oxide sensor 48, 50 is used, it is preferred that the sensors are arranged in a serial configuration, with the heated metal oxide sensor(s) 48, 50 being provided as the final sensor(s) in the series, to increase the likelihood that any viruses or other microbiological contaminants present in the volatile compounds produced by the separating stage will be destroyed prior to being expelled from the detection stage 18 through the exhaust port.

The apparatus 10 may be provided as an integrated multi-purpose device which is capable of analysing different types of sample to diagnose a variety of different conditions. For example, in one mode the apparatus 10 may be configured to diagnose a gastrointestinal condition such as *C. difficile* by analysing a stool sample. In a second mode the apparatus 10 may be configured to analyse a stool sample to diagnose a range of gastrointestinal conditions such as *C. difficile*, ulcerative colitis, colorectal cancer or the like. In a third mode of operation, the apparatus 10 may be configured to analyse a urine sample to diagnose prostate cancer.

It will be appreciated that different conditions are likely to produce different traces or profiles of compounds in samples, and thus in order to produce a diagnosis quickly the apparatus 10 may store a plurality of known traces or profiles from previously-diagnosed samples containing particular volatile compounds or combinations of volatile compounds which are indicative of particular diseases in the storage 26. An appropriate trace or profile can be recalled when necessary for a particular type of analysis or diagnosis. In the example described above a first trace or profile from a sample taken from a patient previously diagnosed as having *C. difficile* may be stored in the storage device 26, along with a second trace or profile which may be a composite trace or an amalgamation of traces or profiles from samples taken from patients previously diagnosed as having a range of conditions such as *C. difficile*, ulcerative colitis, colorectal cancer and the like. A third trace or profile from a sample taken from a patient previously diagnosed as having prostate cancer may also be stored in the storage device 26. Thus, an appropriate trace or profile may be selected according to the analysis or diagnosis being performed, with the trace produced by the sample from the patient being compared to the stored trace to produce a diagnosis.

Additionally or alternatively, different ANNs may be stored in the storage device 26 or in memory of the processor 20 or the control system 24, with each ANN being trained to diagnose a particular condition or range of conditions. This, an appropriate ANN may be selected according to the analysis or diagnosis being performed.

This ability to store and recall different traces and/or ANNs gives the apparatus 10 great flexibility as it allows a single device to be used to diagnose a range of conditions. Additionally, the apparatus 10 can be updated with revised traces and ANNs as improved data is obtained and as new compounds or combinations of compounds which are indicative of particular conditions are discovered. Thus, the apparatus 10 is expandable to meet future diagnostic requirements.

The foregoing description presents exemplary embodiments of the apparatus of the present invention. For the sake of completeness two prototype systems used by the applicant in the development of the apparatus of the present invention will now be described. It will be appreciated that these prototype systems also constitute embodiments of the apparatus of the present invention.

The first prototype apparatus comprises a gas chromatography oven with an injection port into which samples of gas collected from patient samples, such as stool samples, can be injected. Gas is collected from the samples in a separate process in which the samples are heated in headspace vials having an integrated septum through which headspace gas can be used using a gas tight syringe. The headspace gas can then be injected directly into the gas chromatography oven.

A separation stage of this first prototype apparatus uses two commercially-available 30 metre capillary columns with an internal diameter of 0.32 mm an a stationary phase film thickness of 4 μm are interfaced to the injection port using push fit glass connectors and two pieces of silica guard column, to provide four separate outlets of the separation stage. Three of the outlets are interfaced to a sensor array (which is described in detail below), whilst the fourth is interfaced to a conventional flame ionisation detector (FID) which is integral to the gas chromatography oven. A pump is provided to pump blended dry cylinder air around this system to transport the gas collected from the samples.

Two types of sensor are used in the sensor array of this system. The first is a metal oxide sensor of the type described in detail above, and the second is an ammonia or amine sensor of the type described in detail above. Two metal oxide sensors are used in the sensor array, with a single ammonia or amine sensor. The ammonia or amine sensor is encased in a light-tight outer casing before being integrated into the sensor array, to ensure that light from sources other than the LED is excluded and thus cannot influence the output of the ammonia or amine sensor.

The sensors are controlled and their signals conditioned by a bespoke control circuit. A hardware feedback loop is provided which maintains the temperature of each of the metal oxide sensors at a predefined value regardless of heat losses. The temperature of the heater of each metal oxide sensor is continually monitored by measuring voltages permitting the resistance of the platinum heater to be calculated, from which the temperature can be derived. Signals output by the sensors (resistance change for heated metal oxide sensors and voltage change for the ammonia or amine sensor) and the sensor heater voltages are conditioned using conditioning circuitry and fed via an analogue to digital converter via a USB connection to a personal computer running custom diagnosis software.

The software provides a scrolling display of resistance or voltage versus time, and a constant update of the sensor temperatures. When a sample is injected a marker with sample information is added to the trace. This marker is used as a 'time zero' reference point for the subsequent calculation of retention time values (see below). The information is saved in a unique file.

Data collected from each sensor from a sample are transformed so that the change in resistance with time (dR/dt) is displayed, in order to facilitate the deconvolution of peaks that elute with similar retention times. Smoothing is also applied to the traces to reduce the effects of electrical noise and a height threshold is applied in order to exclude small baseline fluctuations caused by noise. Data files are saved in Microsoft Excel format. The files contain a series of retention time values (the time taken for specific compounds to elute the columns) and the respective peak area for each sensor. These data files are collected and analysed for five stool types—*Campylobacter*, *C. difficile*, normal (asymptomatic individuals), *Salmonella* and undiagnosed. The software includes an Artificial Neural Network (ANN) for performing this diagnosis.

Input to the ANN is accomplished by dividing the 30 minute (1800 second) time-span of each data acquisition run into 120 consecutive fifteen second segments ('bins'), and integrating the peaks of the differentiated display across each bin, thus creating an array of 120 input bins. The bins are then normalised proportionally such that the largest bin equals 1. The bins then contain a normalised representation of the chromatogram. The software includes an option to make the bins wider so that the bins can overlap by either 5 or 15 seconds, in case peaks span adjacent bins.

The output from the ANN can be selected to have just two channels (e.g. *C. difficile*/Not *C. difficile*), or six channels, one for each disease type plus one for calibration data produced using a sample of ethanol.

In experimental use of the first prototype system, a proportion of the data files was used to train the ANN (training set), and validation of the ANN was undertaken using the remaining data (validation set), as is shown in Table 1 below.

TABLE 1

Numbers of each disease type in the training and validation sets.

| Type | Training set | Validation set |
|---|---|---|
| Normal | 22 | 11 |
| *C. difficile* | 22 | 10 |
| *Campylobacter* | 23 | 9 |
| Ethanol | 7 | 4 |
| *Salmonella* | 15 | 5 |
| Undiagnosed | 7 | 5 |
| Total | 96 | 44 |

In addition to the 120 input bins (input layer of 120 units) and the 2 or 6 outputs (output layer of either 2 or 6 units), the ANN has one or more hidden layers. The number of units in each hidden layer can affect the accuracy of the artificial neural network. As it is not possible to predict the optimum number of units in a hidden layer, it is necessary to test as many combinations as possible. To this end, the software permits the user to automatically create and validate ANNs where the number of units in the hidden layer before the output layer (which is the only hidden layer in single hidden layer networks) is decremented from 120 down to the number of outputs. This was carried out for single hidden layer ANNs using all combinations of the following parameters: height threshold of 0 or 50; area threshold of 0 or 200; 2 outputs or 6 outputs; bin overlaps of 0, 5 or 15 seconds; using either normalised bin areas or binary transformed bin areas (1 if bin area >0, 0 otherwise).

The best ANNs were found to have the following parameters: height threshold=50; area threshold=200; bin overlap=15 seconds; normalised bin areas.

Using these parameters the results for the 6-output network are shown in Table 2, and the results for the 2-output network are shown in Table 3.

TABLE 2

Results from the 6-output network

| Type | Matched | Total | % Correct |
| --- | --- | --- | --- |
| Normal | 8 | 11 | 72.7 |
| C. difficile | 8 | 10 | 80.0 |
| Campylobacter | 4 | 9 | 44.4 |
| Ethanol | 4 | 4 | 100.0 |
| Salmonella | 2 | 5 | 40.0 |
| Undiagnosed | 4 | 5 | 80.0 |
| Total | 30 | 44 | 68.2 |

TABLE 3

Results from the 2-output network

| Type | Matched | Total | % Correct |
| --- | --- | --- | --- |
| Not C. difficile | 29 | 34 | 85.3 |
| C. difficile | 8 | 10 | 80.0 |
| Total | 37 | 44 | 84.1 |

Since *Salmonella* and *Campylobacter* samples are rarely encountered in a hospital setting, the differentiation of patients with *C. difficile* from patients with either diarrhoea of unknown aetiology or patients who may be asymptomatic is most important in relation to the proposed use of the prototype. Therefore, the ANN was trained using the same data set as before (Table 1), but with the ethanol, *Campylobacter* and *Salmonella* samples removed from the training and validation sets. These results are shown in Tables 4 and 5.

TABLE 4

Results from the 2 output network excluding ethanol, *Salmonella* and *Campylobacter* samples from training and validation sets.

| | Matched | No. in validation set | % Correct |
| --- | --- | --- | --- |
| Not C. difficile | 18 | 18 | 100.0 |
| C. difficile | 8 | 10 | 80.0 |
| Total | 26 | 28 | 92.9 |

TABLE 5

Results from the 6 output network excluding ethanol, *Salmonella* and *Campylobacter* samples from the training and validation sets.

| | Matched | No. in validation set | % Correct |
| --- | --- | --- | --- |
| Normal | 9 | 10 | 90.0 |
| C. difficile | 9 | 10 | 90.0 |
| Undiag | 5 | 5 | 100.0 |
| Total | 23 | 25 | 92.0 |

For comparison, neural networks were generated using data obtained from a conventional FID detector, gathered at the same time as the results from the GC Detector unit. The results are shown in Tables 6 and 7 for the 6-output and 2-output networks respectively.

TABLE 6

Results from the 6-output network using data from a FID detector

| Type | Matched | Total | % Correct |
| --- | --- | --- | --- |
| Normal | 7 | 10 | 70.0 |
| C. difficile | 4 | 10 | 40.0 |
| Campylobacter | 1 | 9 | 11.1 |
| Ethanol | 3 | 4 | 75.0 |
| Salmonella | 1 | 6 | 16.7 |
| Undiagnosed | 4 | 5 | 80.0 |
| Total | 20 | 44 | 45.5 |

TABLE 7

Results from the 2-output network using data from a FID detector

| Type | Matched | Total | % Correct |
| --- | --- | --- | --- |
| Not C. difficile | 25 | 34 | 73.5 |
| C. difficile | 4 | 10 | 40.0 |
| Total | 29 | 44 | 65.9 |

As can be seen from the tables above, networks generated using data from the prototype system give more accurate decisions than networks generated using the FID data.

The second prototype system is similar to the first, but uses a commercially available multicapillary column of 50 cm in length and having 1200 capillaries of 4 µm internal diameter and a stationary phase film thickness of 0.2 µm in the separation stage. A pump is provided to pump laboratory air into the multicapillary column to transport the gas collected from the samples, with the laboratory air being filtered by charcoal filters to remove any contaminants from the laboratory air prior to entry into the multicapillary column. An outlet of the multicapillary column is interfaced directly to a heated metal oxide sensor of the type described above, which operates at a temperature of 450° C.

The heated metal oxide sensor is controlled and its signals conditioned by a bespoke control circuit. A hardware feedback loop is provided which maintains the temperature of the metal oxide sensor at a predefined value regardless of heat losses. The temperature of the heater of the metal oxide sensor is continually monitored by measuring voltages permitting the resistance of the platinum heater to be calculated, from which the temperature can be derived. The resistance change signal output by the sensor and the sensor heater voltage is conditioned using conditioning circuitry and fed via an analogue to digital converter via a USB connection to a personal computer running custom diagnosis software.

The software provides a scrolling display of resistance or voltage versus time, and a constant update of the sensor temperatures. When a sample is injected a marker with sample information is added to the trace. This marker is used as a 'time zero' reference point for the subsequent calculation of retention time values (see below). The information is saved in a unique file.

Data collected from the sensor from a sample are transformed so that the change in resistance with time (dR/dt) is displayed, in order to facilitate the deconvolution of peaks that elute with similar retention times. Smoothing is also applied to the traces to reduce the effects of electrical noise and a height threshold is applied in order to exclude small baseline fluctuations caused by noise. Data files are saved in Microsoft Excel format. The files contain a series of retention time values (the time taken for specific compounds to elute the columns) and the respective peak area for each sensor. These data files are collected and analysed for four stool types—*Campylobacter, C. difficile*, normal (asymptomatic individuals) and undiagnosed. The software includes an Artificial Neural Network (ANN) for performing this diagnosis.

Input to the ANN is accomplished by dividing the 10 minute (600 second) time-span of each data acquisition run into 40 consecutive fifteen second segments ('bins'), and integrating the peaks of the differentiated display across each bin, thus creating an array of 40 input bins. The bins are then normalised proportionally such that the largest bin equals 1. The bins then contain a normalised representation of the chromatogram. The software includes an option to make the bins wider so that the bins can overlap by either 5 or 15 seconds, in case peaks span adjacent bins.

The output from the ANN can be selected to have just two channels (*C. difficile*/Not *C. difficile*), or five channels, one for each disease type plus one for calibration data produced using an ethanol sample.

In experimental use of the second prototype a proportion of the data files was used to train the ANN (training set); validation of the ANN was undertaken using the remaining data (validation set), as shown in Table 8 below.

TABLE 8

Samples used in the training and validation of the second prototype with multicapillary column

| Sample | Total | Training set | Validation set |
|---|---|---|---|
| Normal | 14 | 7 | 7 |
| *C. difficile* | 26 | 13 | 13 |
| Campylobacter | 11 | 5 | 6 |
| Ethanol | 6 | 3 | 3 |
| *Salmonella* | 0 | 0 | 0 |
| Undiagnosed | 7 | 3 | 4 |
| Total | 64 | 31 | 33 |

Table 9 below shows the results obtained with a 2 output ANN (*C. difficile*/Not *C. difficile*) with either 1 or 2 hidden layers. The overall correct classification of samples was 82% if 2 hidden layers were utilised in the ANN. This compares to an overall classification of only 73% if 1 hidden layer was utilised. These results demonstrate that second prototype utilising a short microcapillary column is able to deliver disease diagnosis results in 10 minutes.

TABLE 9

The classification of the validation set using a 2 output ANN with either 1 or 2 hidden layers.

| ANN details | No. units in Hidden Layer | Type | Matched | Total | % Correct |
|---|---|---|---|---|---|
| One hidden layer 40 × 15 sec Bins, No overlap, Threshold 50, Area Threshold 0 | 70 | Not *C. difficile* | 14 | 20 | 70.0 |
| | | *C. difficile* | 10 | 13 | 76.9 |
| | | Total | 24 | 33 | 72.7 |
| Two hidden layers 40 × 15 sec Bin No overlap, Threshold 50 Area Threshold 0 | 70, 107 | Not *C. difficile* | 17 | 20 | 85.0 |
| | | *C. difficile* | 10 | 13 | 76.9 |
| | | Total | 27 | 33 | 81.8 |

Exemplary applications of the apparatus 10 will now be described with reference to the results of experiments carried out by the present applicant using a prototype of the apparatus 10.

Figure 11:
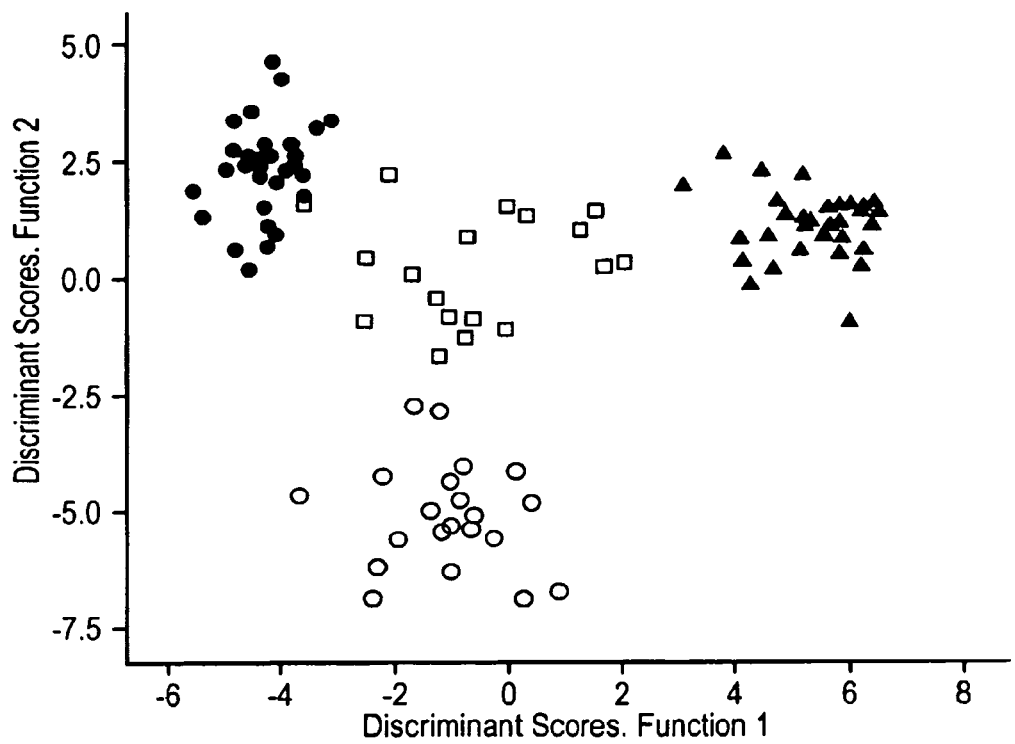
FIG. 11 is a graph showing the results of a discriminant analysis performed on the results of analysis of stool samples using a prototype diagnostic apparatus.

In a first experiment, the prototype was used to diagnose *C. difficile* from a stool sample provided by a patient. In this experiment healthy stool samples and stool samples from patients previously diagnosed with *C. difficile* and with ulcerative colitis were analysed using the prototype apparatus and volatile compounds present in each of the sample types were collated and subjected to a discriminant analysis, the results of which are shown in the graph of FIG. 11. It can clearly be seen from this graph that the compounds found in stool samples from patients diagnosed with *C. difficile* fall into a distinct grouping, and from this information the apparatus 10 can be configured to diagnose *C. difficile* by analysing stool samples, either by direct comparison with a known profile for stool containing compounds indicative of *C. difficile*, or by implementing an ANN trained with data collected from samples taken from patient diagnosed with *C. difficile*.

In a second experiment, the prototype used in the first experiment was used to analyse urine samples provided by two healthy volunteers to produce traces indicative of different volatile compounds found in the samples. Gas was evolved from the samples and passed through the detection stage to produce the traces.

Two methods were used to extract volatile compounds from the gas evolved from the urine samples. In the first method air was extracted from a headspace above the urine sample, whereas in the second method an SPME fibre was exposed to the headspace above the urine sample and was subsequently inserted into the injection port of the gas chromatography oven for desorption and subsequent analysis. In both methods the urine samples were heated to approximately 60° C. prior to the extraction of the headspace air or exposure of the SPME fibre to the headspace air, to promote the release of volatile compounds from the urine samples. The gas chromatography oven was pre-heated to a temperature of 30° C., which temperature was held for six minutes following the injection of the headspace air or SPME fibre into the oven. The temperature of the gas chromatography oven was subsequently raised by 5° C. per minute until a final temperature of 100° C. was reached. The temperature was held at 100° C. for 40 minutes, giving a total run time of 60 minutes. In both methods, three samples were analysed in parallel, with a first 6 ml urine sample being acidified with 1 ml of sulphuric acid (1M), second 6 ml urine sample being basified with 0.5 ml of sodium hydroxide (0.5M) and a third 6 ml sample being treated with an equivalent quantity of deionised water. The acidified and basified samples produced more volatile compounds than the untreated sample.

Table 10 below shows the results of the analysis of the urine samples from the healthy volunteers HV1 and HV2 using the first method. It will be noted that volatile compounds were detected by the detection stage 18 at 45 distinct retention times, indicating the presence in the urine samples of up to 45 volatile compounds. Additionally, more volatile compounds were detected for the acidified samples than for the basified samples and the untreated samples.

TABLE 10

| | RT | HV1 untreated | HV1 acidified | HV1 basified | HV2 untreated | HV2 acidified | HV2 basified |
|---|---|---|---|---|---|---|---|
| 1 | 0.92 | | x | | | | |
| 2 | 1.07 | x | | x | | x | |
| 3 | 1.14 | | x | | x | | x |
| 4 | 1.60 | x | x | | x | x | |
| 5 | 1.80 | x | x | | | x | |
| 6 | 2.28 | x | | x | | | |
| 7 | 4.54 | | | x | | | |
| 8 | 4.85 | x | x | | | x | |
| 9 | 5.12 | | | x | x | | |
| 10 | 5.24 | | x | | | | |
| 11 | 5.44 | | x | | | | |
| 12 | 5.80 | | | | | | x |
| 13 | 6.04 | | x | | | | |
| 14 | 6.57 | | x | | | | |
| 15 | 8.50 | x | x | x | | | |
| 16 | 9.20 | | x | | | | |
| 17 | 9.75 | x | x | x | | | |
| 18 | 10.72 | | x | x | | | |
| 19 | 10.84 | x | | | | | |
| 20 | 11.61 | | x | | | | |
| 21 | 13.14 | x | x | | x | x | |
| 22 | 13.79 | x | | x | | | |
| 23 | 14.74 | | x | | | | |
| 24 | 15.56 | | x | | | | |
| 25 | 15.99 | | x | x | | x | |
| 26 | 16.05 | x | | | | | |
| 27 | 16.32 | | x | | | | |
| 28 | 17.02 | x | x | x | | | |
| 29 | 18.10 | x | | | | | |
| 30 | 18.50 | | x | | | | |
| 31 | 19.29 | x | | | | x | |
| 32 | 19.66 | x | x | | | x | |
| 33 | 21.47 | | x | x | | | |
| 34 | 22.79 | | x | | | | |
| 35 | 23.44 | | x | | | | x |
| 36 | 23.98 | | x | | | | |
| 37 | 24.42 | | x | | | x | |
| 38 | 24.69 | x | | | | | |
| 39 | 25.57 | x | | | | | |
| 40 | 27.06 | x | | | | | |
| 41 | 29.39 | | x | | | x | |
| 42 | 36.24 | | x | | | | |
| 43 | 37.96 | x | | | | | |
| 44 | 58.80 | | | x | | | |
| 45 | 59.61 | x | | | | | |
| Total | | 20 | 29 | 13 | 4 | 9 | 3 |

Figure 12:
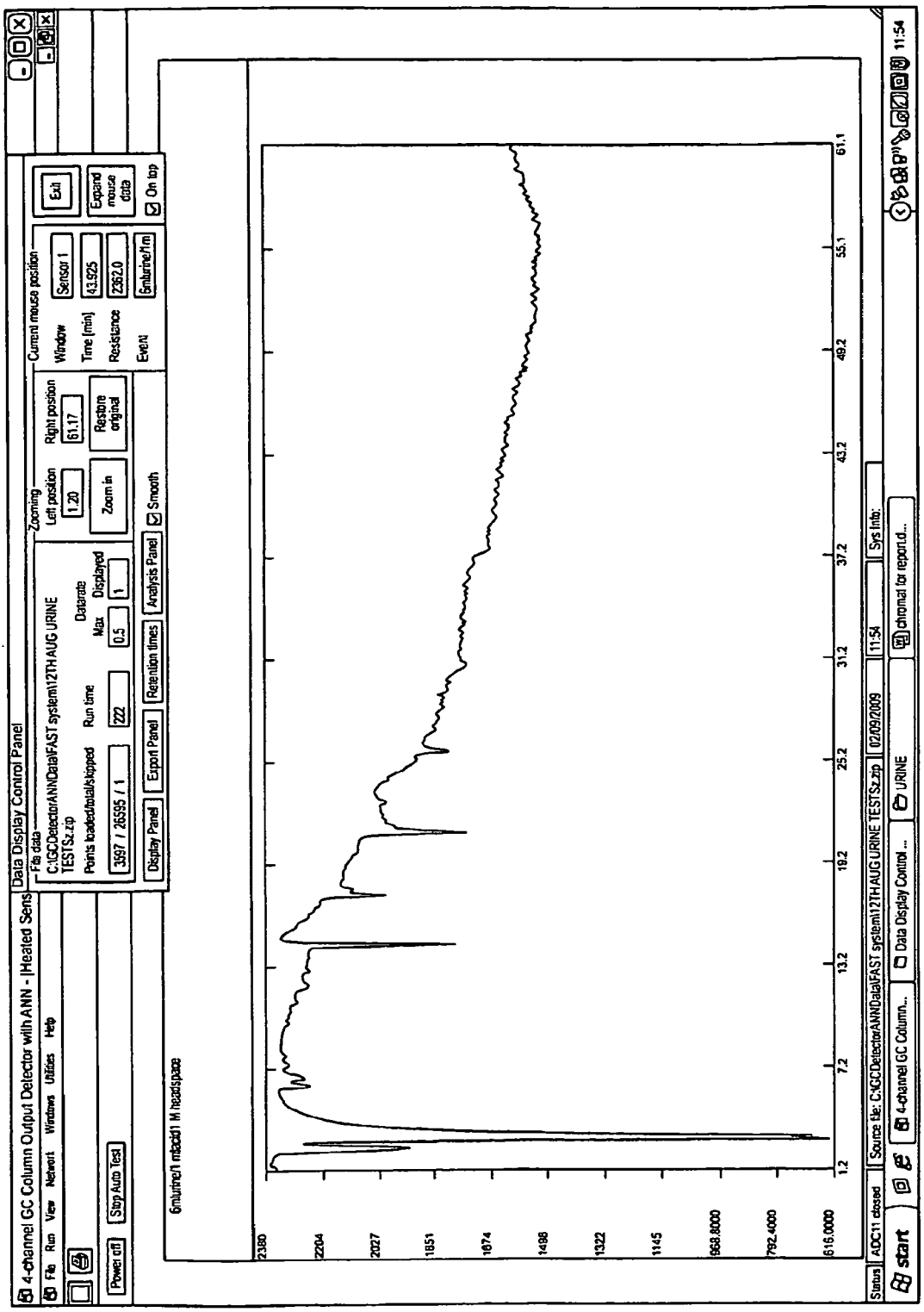
FIG. 12 is a screen shot showing the results of an analysis of a fresh untreated urine sample produced using a prototype diagnostic apparatus.
Figure 13:
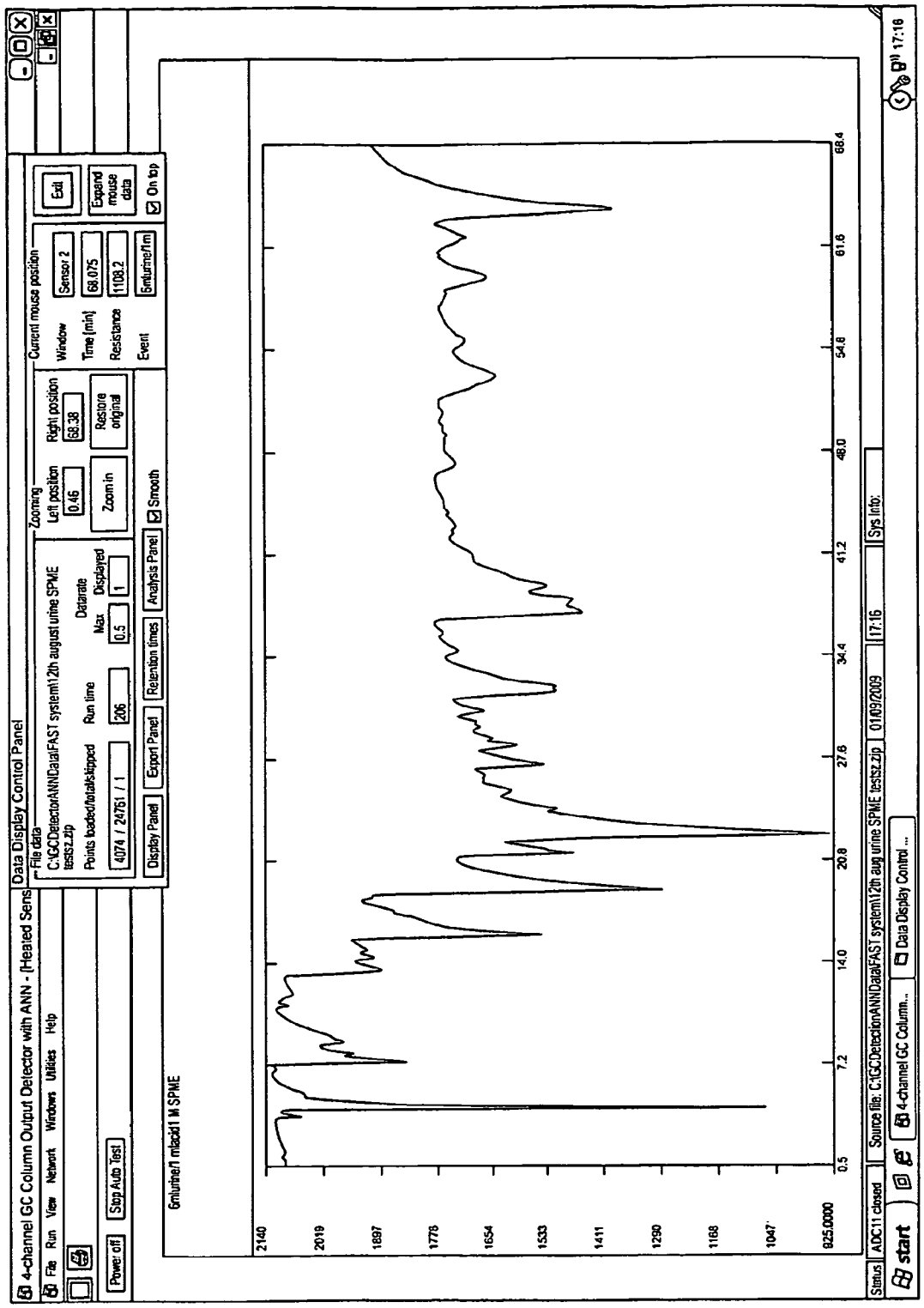
FIG. 13 is a screen shot showing the results of an analysis of an acidified urine sample produced using the prototype diagnostic apparatus.

Table 11 below shows the results of the analysis of the urine samples provided by the healthy volunteers HV1 and HV2 using the second method. With this method volatile compounds were detected by the detection stage 18 at 90 distinct retention times, indicating the presence in the urine samples of up to 90 volatile compounds. As before, more volatile compounds were detected for the acidified samples than for the basified samples and the untreated samples, as is illustrated in FIGS. 12 and 13, which are screenshots showing the results of the analysis using the second method of the untreated urine sample and the acidified urine sample respectively.

TABLE 11

| | RT | HV1 untreated | HV1 acidified | HV1 basified | HV2 untreated | HV2 acidified | HV2 basified |
|---|---|---|---|---|---|---|---|
| 1 | 1.12 | x | x | x | x | x | x |
| 2 | 1.22 | x | | x | | | |
| 3 | 1.58 | x | x | x | x | x | x |
| 4 | 1.96 | x | | | | | |
| 5 | 2.32 | | x | | | | x |
| 6 | 2.54 | x | | x | | | |
| 7 | 3.02 | | | x | | | |
| 8 | 3.23 | | | | | | x |
| 9 | 4.07 | | x | x | | | |
| 10 | 4.40 | | | | | x | |
| 11 | 4.80 | | x | | | | x |
| 12 | 5.19 | | x | x | | | |
| 13 | 6.00 | | x | | | x | |
| 14 | 6.29 | | x | | | | |
| 15 | 6.90 | | | x | | | |
| 16 | 8.24 | | | | | | x |
| 17 | 8.39 | | x | | | | |
| 18 | 8.85 | | | x | | x | x |
| 19 | 9.11 | x | x | | | | |
| 20 | 10.74 | x | x | x | | x | |
| 21 | 11.60 | | x | | | | |
| 22 | 12.13 | | x | | | | |
| 23 | 12.77 | x | | | | | |
| 24 | 12.95 | | | | | | x |
| 25 | 13.11 | x | x | x | | x | |
| 26 | 13.38 | x | | | | | |
| 27 | 13.80 | x | | x | x | | |
| 28 | 14.09 | | x | | | | |
| 29 | 14.24 | | | x | | | |
| 30 | 14.74 | | x | x | | | |
| 31 | 15.24 | x | | | | | |
| 32 | 15.57 | | x | | | | |
| 33 | 15.71 | | | | | | x |
| 34 | 15.94 | | | x | | x | |
| 35 | 16.15 | x | x | | | | x |
| 36 | 16.33 | | x | | x | | |
| 37 | 16.83 | | | | | | x |
| 38 | 17.78 | x | | | | | |
| 39 | 18.55 | x | | x | | x | |
| 40 | 18.78 | | x | | | | |
| 41 | 18.97 | | | x | | | |
| 42 | 19.33 | x | | | | x | |
| 43 | 19.73 | x | | x | | x | |
| 44 | 20.35 | x | | x | x | | x |
| 45 | 21.12 | | | | | | x |
| 46 | 21.48 | | x | x | | | |
| 47 | 22.70 | | x | | | x | |
| 48 | 23.19 | x | | | | | |
| 49 | 23.38 | | | x | | | |
| 50 | 23.78 | | x | | | | x |
| 51 | 24.46 | | x | x | | x | |
| 52 | 24.73 | | x | | | | |
| 53 | 25.45 | x | | | | x | |
| 54 | 25.69 | | x | | | | |
| 55 | 26.16 | | x | | | x | |
| 56 | 26.93 | | x | | | | |
| 57 | 27.17 | | | | | | x |
| 58 | 27.26 | | x | | | | |
| 59 | 27.48 | x | | | | | |
| 60 | 28.04 | | x | | | x | |
| 61 | 29.32 | | x | | | | |
| 62 | 29.60 | | x | x | x | x | |
| 63 | 30.25 | x | x | x | | | x |
| 64 | 32.17 | | x | | | | x |

TABLE 11-continued

| | | HV1 | | | HV2 | |
|---|---|---|---|---|---|---|
| RT | un-treated | acidified | basified | un-treated | acidified | basified |
| 65 | 33.18 | | x | | | |
| 66 | 34.52 | | x | x | | x |
| 67 | 34.90 | x | | | | |
| 68 | 34.94 | x | | | | |
| 69 | 35.32 | | x | | | |
| 70 | 36.30 | | x | x | | |
| 71 | 36.60 | | | | | x |
| 72 | 37.30 | | x | | | |
| 73 | 38.07 | | | | | x |
| 74 | 38.45 | | x | | | |
| 75 | 39.11 | | | x | | |
| 76 | 40.33 | | x | | | |
| 77 | 40.97 | | | | | x |
| 78 | 41.28 | | x | | | |
| 79 | 44.43 | | x | | | |
| 80 | 45.83 | | x | | | |
| 81 | 46.33 | | x | | | |
| 82 | 47.43 | | | | | x |
| 83 | 47.80 | | x | | | |
| 84 | 48.17 | | | x | | |
| 85 | 50.23 | | x | | | |
| 86 | 52.66 | | x | | | |
| 87 | 55.19 | x | | x | | |
| 88 | 56.70 | | x | | x | |
| 89 | 59.54 | x | x | x | | |
| 90 | 61.24 | | x | x | x | |
| Total | 26 | 53 | 32 | 7 | 18 | 21 |

These results demonstrate that the apparatus 10 can be used to diagnose disease by analysing urine samples to detect compounds which may be indicative of disease, in the same manner as is described above in relation to the detection of disease by analysing stool samples.

In a further experiment, the prototype used in the first two experiments was used to analyse 52 urine samples, 17 of which were taken from patients diagnosed by biopsy with prostate cancer, and the remaining 35 of which were taken from patients where biopsy results for prostate cancer were negative.

In this experiment the ANN was trained using 11 urine samples from patients diagnosed by biopsy with prostate cancer and 22 samples where biopsy results for prostate cancer were negative to provide training data. After training of the ANN the 52 samples were analysed using the method described below.

For each sample an aliquot of fresh urine, 6 ml, was transferred to a headspace vial and was treated with 1 ml of sulphuric acid (1M). The mixture was left to equilibrate at room temperature for 30 minutes and was thereafter heated for 20 minutes at 60° C. before extraction of 2 cm³ of headspace air. Following extraction the headspace air was immediately injected into the injection port (100° C.) of the gas chromatography oven 12 for analysis.

The gas chromatography oven 12 was started at a temperature of 30° C. and held for 6 minutes. Then a ramp of 5° C. per minute was applied until a final temperature of 100° C. was reached. The temperature was held at 100° C. for 40 minutes giving a total run time of 60 minutes.

Increasing the temperature of the oven increases the number of peaks detected by the sensor system. This step is necessary for detecting volatile compounds in urine as the concentrations are lower in stool samples.

The ANN used in this experiment gave 83% positive identification of prostate cancer samples and 69% positive identification of negative samples. Overall classification of samples was 74%.

The invention claimed is:

1. A method of diagnosing disease by analysing a gas obtained from a faeces or urine sample of a patient, the method comprising the steps of:
   (i) heating to about 60° C., using a sample heater, the faeces or urine sample to release a gas from the sample;
   (ii) supplying the gas released from the heated sample in step (i) to one or more heated separation columns in a gas chromatography oven;
   (iii) separating the gas supplied in step (ii) into component parts by heating the gas in the one or more heated separation columns in the gas chromatography oven;
   (iv) directing the component parts of the gas from step (iii) towards a sensor arrangement, the sensor arrangement being configured to detect a compound which may be indicative of disease, the sensor comprising:
      a metal oxide element comprising a mixture of powdered zinc oxide and powdered tin oxide; and
      a sensor heater configured to heat the metal oxide element;
      wherein the sensor is configured to apply a voltage to the metal oxide element to produce current flow in the metal oxide element;
   (v) maintaining, using the sensor heater, a temperature of the metal oxide element during sensing in step (iv) at between 425° C. and 500° C.; and
   (vi) processing a signal indicative of the current flow by the sensor arrangement to produce an indication capable of providing a diagnosis.

2. A method according to claim 1 wherein the step of separating the gas comprises passing the gas through a separating element comprising a multi-capillary column.

3. A method according to claim 1 wherein the step of separating the gas comprises passing the gas through a separating element comprising a single-capillary column or a plurality of single-capillary columns.

4. A method according to claim 1 wherein the sensor arrangement comprises two or more sensors arranged in a serial configuration.

5. A method according to claim 1 wherein the sensor arrangement comprises two or more sensors arranged in a parallel configuration.

6. A method according to claim 1 wherein the sensor arrangement is configured to detect one or more volatile compounds present in the gas.

7. A method according to claim 6 wherein the sensor arrangement is configured to generate a signal indicative of the elution time of a volatile compound in the sample.

8. A method according to claim 7 wherein the step of processing the signal output by the sensor arrangement comprises comparing the signal generated by the sensor arrangement to a known profile from one or more previously-diagnosed samples.

9. A method according to claim 1 wherein the step of processing the signal output by the sensor arrangement comprises processing the signal using an artificial neural network to provide the diagnosis.

* * * * *